United States Patent [19]

Smith et al.

[11] Patent Number: 5,223,421
[45] Date of Patent: Jun. 29, 1993

[54] IDENTIFICATION OF METHIONINE Nα-ACETYLTRANSFERASE

[75] Inventors: John A. Smith, Brookline, Mass.; Fang-Jen S. Lee, North Bethesda, Md.

[73] Assignee: The General Hospital Corporation, Boston, Mass.

[21] Appl. No.: 597,720

[22] Filed: Oct. 16, 1990

Related U.S. Application Data

[63] Continuation-in-part of Ser. No. 473,276, Jan. 31, 1990, abandoned, and a continuation-in-part of Ser. No. 426,382, Oct. 25, 1989, abandoned.

[51] Int. Cl.$^5$ .......................... C12N 9/10; C12N 1/18; C12N 11/00; C12R 1/865
[52] U.S. Cl. ..................................... 435/193; 435/255; 435/256; 435/803; 435/814; 435/815; 435/942
[58] Field of Search ....................... 435/69.1, 193, 255, 435/256, 942

[56] References Cited

PUBLICATIONS

Lee, F-J. S., et al., *The Journal of Biological Chemistry* 265:3603-3606 (1990).
Tsunasawa, S., et al., *The Journal of Biological Chemistry* 260:5382-5391 (1985).
Lee, F-J. S. et al., *The Journal of Biological Chemistry* 263:14948-14955 (1988).
Lee, F-J. S. et al., *The Journal of Biological Chemistry* 264:12339-12343 (1989).
Tsunasawa, S. et al., *Methods In Enzymology* 106:165-170 (1984).
Driessen, H. P. C., et al., *CRC Critical Reviews in Biochemistry* 18:281-325 (1985).
Wold, F., *Trends Biochem. Sci.* 9:256-257 (1984).
Pestana, A. et al., *Biochemistry* 14:1404-1412 (1975).
Yamada, R. et al., *1st Sym. Protein Soc.* 625:34 (1987).
O'Donohue, T. L., *The Journal of Biological Chemistry* 258:2163-2167 (1983).
Woodford, T. A. et al., *The Journal of Biological Chemistry* 254:4993-4999 (1979).
Arfin, S. M., et al., *Biochemistry* 27:7979-7984 (1988).
Smith, J. A. et al., *Banbury Report* 28:69-75 (1988).
Kamitani, K. et al., *The Journal of Biological Chemistry* 264:13188-13193 (1989).
Mullen, J. R. et al., *The EMBO Journal* 8:2067-2075 (1989).
Lee, F-J. S. et al., *Journal of Bacteriology* 171:5795-5802 (1989).
Lee, F-J. S. et al., *FEBS Lett.* 256:139-142 (1989).
Albelda et al. *FASEB J.* 4:2868-2880 (1990).
Hynes, *Cell* 49:549-554 (1987).
Ruoslahti, *J. Clin. Invest*, 87: 1-5 (1991).
Fitzgerald et al., *J. Biol. Chem.*, 262:3936-3939 (1987).
Hogervorst et al., *EMBO J.*, 9:765-770 (1990).
Kishimoto et al., *Cell*, 48:681-690 (1987).
McLean et al., *J. Biol. Chem.*, 265:17126-17131 (1990).
Ramaswamy et al., *EMBO J.* 9:1561-1568 (1990).
Sheppard et al., *J. Biol. Chem*, 265:11502-11507 (1990).
Suzuki and Naitoh, *EMBO J.* 9:757-763 (1990).
Tamkun et al., *Cell* 46:271-282 (1986).
Yuan et al., *Intl. Immunol.*, 2:1097-1108 (1990).
Halten et al., *Trends. Neurol. Sci.*, 13:179-184 (1990).
Jessell, *Neuron*, 1:3-13 (1988).

(List continued on next page.)

*Primary Examiner*—Robert A. Wax
*Assistant Examiner*—Dian C. Jacobson
*Attorney, Agent, or Firm*—Sterne, Kessler, Goldstein & Fox

[57] ABSTRACT

A methionine Nα-acetyltransferase enzyme has been identified in yeast. The existence of the enzyme defines a gene for methionine Nα-acetyltransferase which may be cloned and altered. Cells expressing the normal or variant forms of this enzyme are valuable tools for determining the amino acid sequence of uncharacterized proteins. Such cells are also valuable tools for expressing a recombinant protein lacking an acetyl group at its α-amino group.

6 Claims, 2 Drawing Sheets

PUBLICATIONS

Sanes, *Ann. Rev. Neurosci*, 12:491–516 (1989).
Plantefaber and Hynes *Cell*, 56:281–290 (1989).
Saga et al., *Cancer Res.*, 48:5510–5513 (1988).
Bodary and McLean, *J. Biol. Chem.*, 265:5938–5941 (1990).
Fitzgerald and Phillips, *Molecular Biology, Immunology, Biochemistry and Pathology* pp. 387–418 (Alan R. Liss, NY 1988).
Hemler, *Ann Rev. Immunol.*, 8:365–400 (1990).
Horton, *Int. Exp. Pathol.*, 71:741–759 (1990).
Kieffer and Phillips *Ann. Rev. Cell Biol.*, 6:329–357 (1990).
Kajiji et al., *EMBO J*, 8(3):673–680 (1989).
Phillips et al., *Blood*, 71(4):831–843 (1988).
Bossy et al., *Biochemistry*, 29:10191–10198 (1990).
Chuong, *Experientia*, 46:892–899 (1990).
Rathgen et al., *Trends in Neurosciences* 11(5):183–184 (1988).

IDENTIFICATION OF METHIONINE Nα-ACETYLTRANSFERASE

CROSS-REFERENCE TO RELATED APPLICATIONS

This application is a continuation-in-part of U.S. patent application Ser. Nos. 07/473,276 (filed on Jan. 31, 1990, now abandoned) and which is a continuation-in-part of 07/426,382 (filed on Oct. 25, 1989, now abandoned), both herein incorporated by reference.

FIELD OF THE INVENTION

The invention pertains to an Nα-Acetyltransferase enzyme which is capable of acetylating methionine residues of a peptide or protein, and to recombinant molecules which encode this enzyme, and to host cells which express the enzyme. The invention also concerns the purification of the enzyme from various hosts, such as the yeast, *Saccharomyces cerevisiae*. Additionally, the invention concerns the uses of the enzyme in research and in industrial applications.

BACKGROUND OF THE INVENTION

Amino terminal acylation is an important co-translational modification of proteins in prokaryotic and eukaryotic cells. Although formyl, pyruvoyl, α-ketobutyryl, glycosyl, glucuronyl, α-aminoacyl, p-glutamyl, myristoyl, and acetyl are well-known Nα-acylating groups, it is clear that acetylation is the most common chemical modification of the α-NH$_2$ group of eukaryotic proteins (Tsunasawa, S., et al., *Methods Enzymol* 106:165–170 (1984); Driessen, H. P. C., et al., *CRC Crit. Rev. Biochem* 18:281–325 (1985)).

Nα-acetylation plays a role in normal eukaryotic translation and processing (Wold, F., *Trends Biochem. Sci.* 9:256–257, (1984)) and protects against proteolytic degradation (Jornvall, H., *J. Theor. Biol.* 55:1–12 (1975); Rubenstein, P., et al., *J. Biol. Chem.* 254:11142–11147 (1979)).

After the discovery that an acetyl moiety was the N-terminal blocking group of tobacco mosaic virus coat protein (Narita, K., et al., *Biochim. Biophys. Acta*, 28:184–191 (1958)) and α-melanocyte-stimulating peptide (Harris, J. I., et al., *Biochem J.* 71:451–459 (1959)), a large number of proteins from various organisms have been shown to possess acetylated N-terminal residues (Brown, J. L., et al., *J. Biol. Chem.* 251:1009–1014 (1976); Brown, J. L., et al., *J. Biol. Chem.* 254:1447–1449 (1979)). For example, mouse L-cells and Ehrlich ascites cells have about 80% of their intracellular soluble proteins Nα-acetylated (Brown, J. L., et al., *J. Biol. Chem.* 251:1009–1014 (1976); Brown, J. L., et al., *J. Biol. Chem.* 254:1447–1449 (1979)). In lower eukaryotic organisms, about 50% of the soluble proteins are acetylated (Brown, J. L., Int'l. Congr. Biochem. Abstr. (International Union of Biochemistry, Canada) Vol. 11:90 (1979)). These data demonstrate that the Nα-acetyl group is a very important blocking group. It has been suggested that the biological function of this blocking group may be to protect against premature protein catabolism (Jornvall, H., *J. Theor. Biol* 55:1–12 (1975)) and protein proteolytic degradation (Rubenstein, P. and Deuchler, J., *J. Biol. Chem.* 254:11142 (1979)). However, in mouse L-cells such Nα-acetylation does not apparently have this biological function (Brown, J. L., *J. Biol. Chem.* 254:1447 (1979)).

Although a clear general function for Nα-acetylation has not been assessed with certainty, some specific effects for a small number of proteins have been observed. Nonacetylated NADP-specific glutamate dehydrogenase in a mutant of *Neurospora crassa* is heat-unstable, in contrast to the acetylated form (Siddig et al., *J. Mol. Biol.* 137:125 (1980)). A mutant of *Escherichia coli*, in which ribosomal protein S5 is not acetylated, exhibits thermosensitivity (Cumberlidge, A. G. and Isono, K., *J. Mol. Biol.* 131:169 (1979)). Nα-acetylation of two of the products from the precursor protein proopiomelanocortin has a profound regulatory effect on the biological activity of these polypeptides; the opioid activity of β-endorphin is completely suppressed, while the melanotropic effect of α-MSH is increased if Nα-acetylated (Smyth et al., *Nature* 279:252 (1970); Smyth, D. G. and Zakarian, S., *Nature* 288:613 (1980); and Ramachandran, J. and Li, C. H., *Adv. Enzymol.* 29:391 (1967)). Both acetylated and nonacetylated cytoplasmic actin from cultured Drosophila cells participate in the assembly of microfilaments, the latter, however, with less efficiency (Berger et al., *Biochem. Genet.* 19:321 (1981)). More recently, the rate of protein turnover mediated by the ubiquitin-dependent degradation system was shown to depend on the presence of a free α-NH2 group at the N-terminus of a protein (Hershko et al., *Proc. Nat'l. Acad. Sci. U.S.A* 81:9021–9025 (1984) and Bachmair et al., *Science* 234:179–186 (1986)), suggesting that Nα-acetylation may have a role in impeding protein turnover.

Nα-acetylation is mediated by at least one Nα-acetyltransferase, which catalyzes the transfer of an acetyl group from acetyl coenzyme A to the α-NH$_2$ group of proteins and peptides. Nα-acetyltransferases have previously been demonstrated in *E. coli* (Brot, N., et al., *Arch. Biochem. Biophys.* 155:475–477 (1973)), rat liver (Pestana, A., et al., *Biochemistry* 14:1397–1403 (1975); Pestana, A., et al., *Biochemistry* 14:1404–1412 (1975); Yamada, R., et al., 1st *Symposium of the Protein Society* 625:34 (1987)), rat brain (O'Donohue, T. L., *J. Biol. Chem.* 258:2163–2167 (1983)), rat pituitary (Woodford, T. A., et al., *J. Biol. Chem.* 254:4993–4999 (1979); Pease, K. A., et al., *Arch.Biochem. Biophys.* 212:177–185 (1981); Gembotski, C. C., *J. Biol. Chem.* 257:10501–10509 (1982); Chappell, M. C., et al., *J. Biol. Chem.* 261:1088–1091 (1986)), bovine pituitary (Gembotski, C. C., *J. Biol. Chem.* 257:10501–10509 (1982)), bovine lens (Granger, M., et al., *Proc. Natl. Acad. Sci. USA* 73:3010–3014 (1976)), hen oviduct (Tsunasawa, S., et al., *J. Biochem.* 87:645–650 (1980)), and wheat germ (Kido, H., et al., *Arch. Biochem. Biophys.* 208:95–100 (1981)). Nα-acetyltransferase enzymes from these sources have, however, never been purified more than 40-fold.

SUMMARY OF THE INVENTION

Nα-Acetylation is the major chemical modification of the α-amino group of proteins occurring in eukaryotic cells. Nα-acetylation markedly affects the biological activity of proteins and peptides. Further, the rate of protein turnover mediated by the ubiquitin-dependent degradation system depends on the presence of a free α-amino, and this dependence indicates that Nα-acetylation may play a crucial role in impeding protein turnover.

The transfer of an acetyl group from acetyl-Coenzyme A to the α-amino group of commonly acetylated residues (such as serine, alanine, methionine, glycine and threonine) in proteins was previously believed to be catalyzed by a single $N^\alpha$-acetyltransferase. The present invention reveals that a second $N^\alpha$-acetyltransferase is responsable for the acetylation of methionine residues. The identification of this methionine $N^\alpha$-acetyltransferase provides an explanation for the two distinct classes of $N^\alpha$-acetylated proteins which exist in nature: those whose initiator methionine is acetylated, and those whose penultimate residue is acetylated after cleavage of the initiator methionine.

In detail, the present invention thus concerns a methionine $N^\alpha$-acetyltransferase being substantially free of natural contaminants.

The invention further concerns a cell which expresses an altered methionine $N^\alpha$-acetyltransferase.

The invention also concerns a yeast cell which expresses an altered methionine $N^\alpha$-acetyltransferase, and, in particular, a yeast cell which substantially lacks aaa1 $N^\alpha$-acetyltransferase activity.

The invention also includes a recombinant molecule encoding a methionine $N^\alpha$-acetyltransferase.

The invention also includes a cell which expresses a recombinant molecule encoding a methionine $N^\alpha$-acetyltransferase.

The invention also provides a method for producing a peptide lacking a methionine $N^\alpha$-acetylated amino terminus which comprises expressing the peptide in a yeast cell having a mutation in the yeast methionine $N^\alpha$-actyltransferase gene, wherein the mutation results in the substantial loss of methionine $N^\alpha$-acetyltransferase activity, and renders the cell unable to catalyze the $N^\alpha$-acetylation of the peptide.

The invention also provides a method for determining the amino acid sequence of a peptide or protein which comprises:

A. expressing the peptide or protein in a yeast cell having a mutation in a gene which encodes a methionine $N^\alpha$-acetyltransferase, wherein the mutation results in the substantial loss of methionine $N^\alpha$-acetyltransferase activity, and renders the cell unable to catalyze $N^\alpha$-acetylation of peptides or proteins;

B. recovering the peptide or protein; and

C. determining the amino acid sequence of the peptide or protein.

DESCRIPTION OF THE PREFERRED EMBODIMENTS

Figure 1:
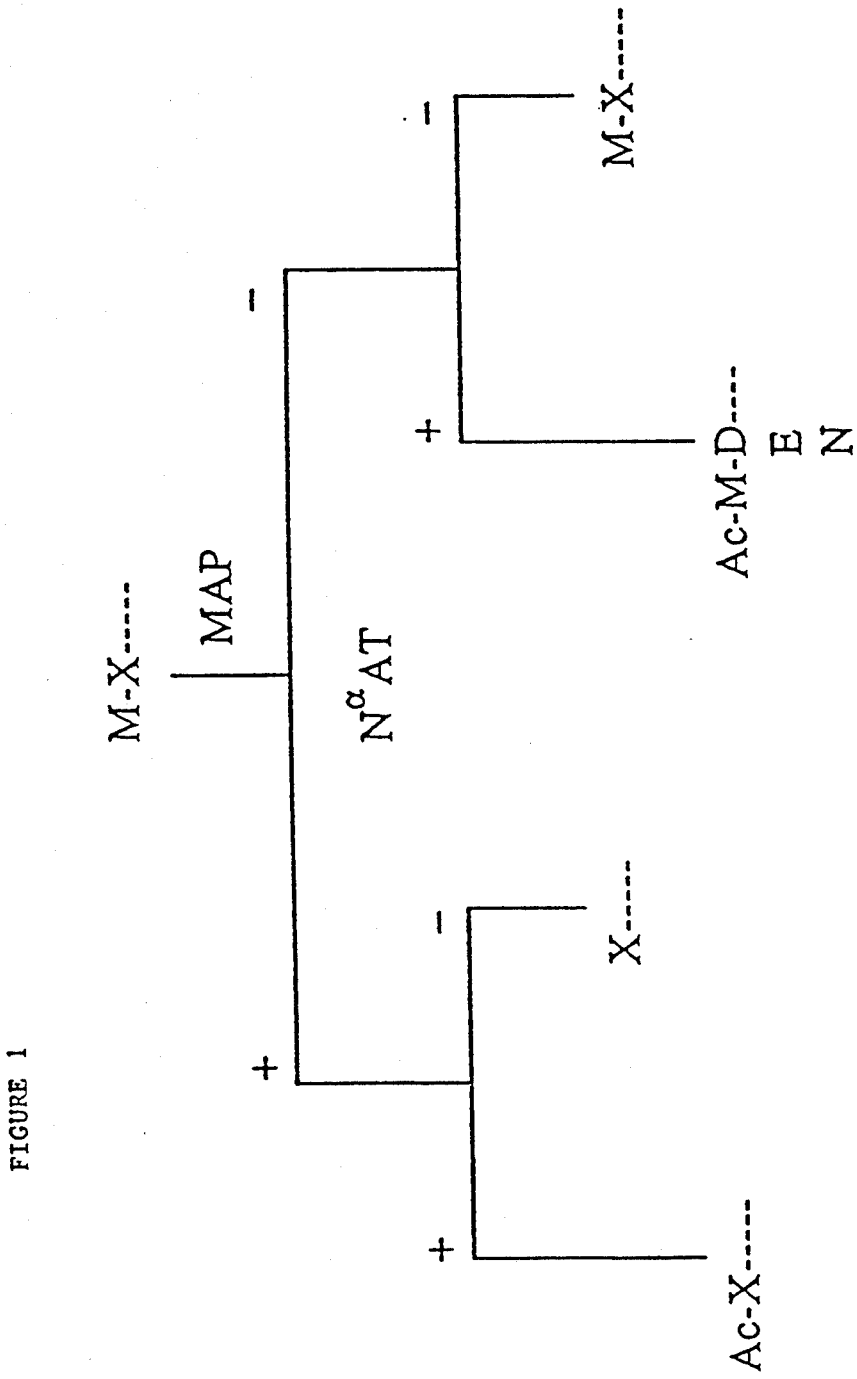
FIG. 1 shows a proposed pathway for the co-translational modification of eukaryotic proteins involving methionine aminopeptidase (MAP) and a single $N^\alpha$-acetyltransferase ($N^\alpha$-AT).

A. $N^\alpha$-acetyltransferases $N^\alpha$-Acetylation is the most common chemical modification of the $\alpha$-amino group at the amino-termini of eukaryotic proteins (Tsunasawa, S., et al., *Methods Enzymol* 106:165 (1984); Driessen, H. P. C., et al., *CRC Crit. Rev. Biochem.* 18:281 (1985); Wold, F., *Trends Biochem. Sci.* 9:256 (1984); Jornvall, H., *J. Theoret. Biol.* 55:1 (1975); Rubenstein, P. et al., *J. Biol. Chem.* 254:11142 (1979)). Narita (Narita, K., *Biochim. Biophys. Acta* 28:184 (1958)) first demonstrated the presence of an $N^\alpha$-acetyl group in the tobacco mosaic virus coat protein, and now it is known that 50–80% of soluble eukaryotic proteins are acetylated (Brown, J. L., et al., *J. Biol. Chem.* 251:1009 (1976); Brown, J. L., *J. Biol. Chem.* 254:1447 (1979); Brown, J. L., Intl. Congress Biochem. Abstr., Vol. 11, International Union of Biochemistry, Canada, p. 90 (1979)). For example, $N^\alpha$-acetylation has been found to have a profound regulatory effect on the biological activity of proopiomelanocortin. The opiod activity of $\beta$-endorphin is completely suppressed, while the melanotropic effect of $\alpha$-melanocyte stimulating hormone is markedly increased (Smyth, D. G. et al., *Nature* 279:252 (1979); Smyth, D. G. et al., *Nature* 288:613 (1980); Ramachandran, J. et al., *Adv. Enzymol.* 29:391 (1967)). Non-acetylated actin participates less efficiently in the assembly of microfilaments than $N^\alpha$-acetylated actin (Berger, E. M. et al., *Biochem Genet.* 19:391 (1981)).

In contrast to normal, non-acetylated hemoglobin, variant hemoglobin Raleigh ($\beta_1$ valine→acetylalanine), minor human fetal hemoglobin $F_1$, and feline hemoglobin with $N^\alpha$-acetylated amino-terminal residues display a decreased affinity for oxygen and a decreased interaction with organic phosphate co-factors (Taketa, F. et al., *J. Biol. Chem.* 246:4471 (1971); Moo-Pen, W. F. et al., *Biochem.* 16:4872 (1977); Bunn, H. F. et al., *J. Clin. Invest.* 49:1088 (1970)).

Further, the rate of protein turnover mediated by the ubiquitin-dependent degradation system depends on the presence of a free $\alpha$-amino group at the amino-terminus of model proteins (Hershko, A., et al., *Proc. Natl. Acad. Sci. USA* 81:7021 (1984); Bachmair, A., et al., *Science* 234:179 (1986); Mayer, A. et al., *Science* 244:1480 (1989)), and this dependence indicates that $N^\alpha$-acetylation may play a crucial role in impeding protein turnover. Thus, $N^\alpha$-acetylation plays important roles in regulating diverse protein functions.

Two distinct classes of $N^\alpha$-acetylated proteins exist: (i) those whose penultimate residue is acetylated after cleavage of the initiator methionine and (ii) those whose initiator methionine is acetylated (Arfin, S. M., et al., *Biochemistry* 27:7979 (1988); Smith, J. A., et al., in *Therapeutic Peptides and Proteins: Assessing the New Technologies*, Marshak, D. R., et al., eds., Cold Spring Harbor Laboratory, Cold Spring Harbor, N.Y., pp. 69–75 (1988))

A proposed pathway for the co-translational modification of eukaryotic proteins involving methionine aminopeptidase (MAP) and a single $n^\alpha$-acetyltransferase ($N^\alpha$-AT), as previously proposed by Arfin and Bradshaw (Arfin, S. M., et al., *Biochemistry* 27:7979 (1988)) is shown in FIG. 1. In the depicted pathway, MAP removes the initiator Met from some but not other proteins and a single $N^\alpha$-AT acetylates certain proteins from each class. The initiator methionine, penultimate residue, and acetyl group at the $\alpha$-amino group are indicated by M, X, and Ac, respectively. The nascent polypeptide is indicated (- - -). The positive (+) and negative (−) actions of the enzymes for the protein substrate is indicated.

The transfer of an acetyl group from acetyl-coenzyme A to the $\alpha$-amino group is catalyzed by $N^\alpha$-acetyltransferase. Recently, $N^\alpha$-acetyltransferases with identical substrate specific were purified from yeast and hen oviduct (Lee, F-J. S., et al., *J. Biol. Chem.* 263:14948

(1988); Kamitani, K., et al., *J. Biol. Chem.* 264:13188 (1989)). The yeast enzyme is encoded by a single gene (AAA1; also called NAT1 (Mullen, J. R., et al., *EMBO J.* 8:2067 (1989); Lee, F.-J. S., et al., *J. Biochem.* 264:12339 (1989), which was disrupted by gene replacement to generate a yeast mutant (aaa1; also called nat1) lacking $N^\alpha$-acetyltransferase activity (Mullen, J. R., et al., *EMBO J.* 8:2067 (1989); Lee, F.-J. S., et al., *J. Bacteriol.* 171:5795–5802 (1989), U.S. Patent Application of John A. Smith, and Fang-Jen S Lee, filed Oct. 25, 1989, entitled "ISOLATION OF STRAINS OF *SACCHAROMYCES CEREVISIAE* HAVING ALTERED $N^\alpha$-ACETYLTRANSFERASE ACTIVITY," which references are incorporated herein by reference). This mutant was sporulation defective, sensitive to heat shock, and a-type mating function defective.

An analysis of soluble proteins from the aaa1 mutant and wild-type yeast strain by two-dimensional gel electrophoresis indicated that only 20% of soluble proteins in the aaa1 mutant were electrophoretically shifted in a manner expected for proteins lacking an $N^\alpha$-acetyl group (Lee, F.-J. S., et al., *FEBS Letters*, 256:139–142 (1989), which reference is incorporated herein by reference). In contrast, approximately 50% of soluble proteins are known to be $N^\alpha$-acetylated (Brown, J. L., et al., *J. Biol. Chem.* 251:1009 (1976); Brown, J. L., *J. Biol. Chem.* 254:1447 (1979); Brown, J. L., Intl. Congress Biochem. Abstr., Vol. 11, International Union of Biochemistry, Canada, p. 90 (1979)). Since the aaa1 mutant lacked the only known $N^\alpha$-acetyltransferase, this finding suggested that an additional $N^\alpha$-acetyltransferase was present in the aaa1 mutant. The present invention derives, in part, from this discovery.

The present invention concerns a methionine $N^\alpha$-acetyltransferase enzyme, or variant thereof, which is "substantially pure" or which has been "substantially purified." As used herein, the terms "substantially pure" or "substantially purified" are intended to be equivalent, and to describe a methionine $N^\alpha$-acetyltransferase which is substantially free of a compound normally associated with the enzyme in its natural state, i.e., a protein, carbohydrate, lipid, etc. The term is further meant to describe a methionine $N^\alpha$-acetyltransferase which is homogeneous by one or more of the assays of purity or homogeneity used by those of skill in the art. For example, a substantially pure methionine $N^\alpha$-acetyltransferase will show constant and reproducible characteristics within standard experimental deviations for parameters such as the following: molecular weight, chromatographic techniques, etc. The term "substantially pure", however, is not meant to exclude artificial or synthetic mixtures of the enzyme with other compounds. The term is also not meant to exclude the presence of impurities which do not interfere with the biological activity of the enzyme, and which may be present, for example, due to incomplete purification.

B. The Cloning of the $N^\alpha$-acetyltransferase Gene

Any of a variety of procedures may be used to clone the *Saccharomyces cerevisiae* $N^\alpha$-acetyltransferase gene of the present invention. One such method entails analyzing a shuttle vector library of cDNA inserts (derived from an $N^\alpha$-acetyltransferase expressing cell) for the presence of an insert which contains the $N^\alpha$-acetyltransferase gene. Such an analysis may be conducted by transfecting cells with the vector and then assaying for $N^\alpha$-acetyltransferase expression. The preferred method for cloning this gene entails determining the amino acid sequence of the $N^\alpha$-acetyltransferase enzyme and using these sequences to design probes capable of hybridizing with $N^\alpha$-acetyltransferase-encoding cDNA. To accomplish this task, one sequences purified $N^\alpha$-acetyltransferase protein or fragments of this protein (obtained, for example, with cyanogen bromide, or with proteases such as papain, chymotrypsin or trypsin (Oike, Y. et al., *J. Biol. Chem.* 257:9751–9758 (1982); Liu, C. et al., *Int. J. Pept. Protein Res.* 21:209–215 (1983)). Preferably, such sequencing is accomplished using automated sequenators. If peptides of more than 10 amino acids are sequenced, the sequence information is generally sufficient to permit one to clone a gene such as the gene for $N^\alpha$-acetyltransferase.

Once the complete molecule, or one or more suitable peptide fragments of the molecule, have been sequenced, the DNA sequences capable of encoding them are examined. Because the genetic code is degenerate, more than one codon may be used to encode a particular amino acid (Watson, J. D., *In: Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon. Although occasionally such amino acid sequences may be encoded by only a single oligonucleotide, frequently the amino acid sequence can be encoded by any of a set of similar oligonucleotides. Importantly, whereas all of the members of the set contain oligonucleotides which are capable of encoding the peptide fragment and, thus, potentially contain the same nucleotide sequence as the gene which encodes the peptide fragment, only one member of the set contains a nucleotide sequence that is identical to the nucleotide sequence of this gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

In a manner exactly analogous to that described above, one may employ an oligonucleotide (or set of oligonucleotides) which has a nucleotide sequence that is complementary to the oligonucleotide sequence or set of sequences that is capable of encoding the peptide fragment.

A suitable oligonucleotide, or set of oligonucleotides which is capable of encoding a fragment of the $N^\alpha$-acetyltransferase gene (or which is complementary to such an oligonucleotide, or set of oligonucleotides) is identified (using the above-described procedure), synthesized, and hybridized, by means well known in the art, against a DNA or, more preferably, a cDNA preparation derived from yeast cells which are capable of expressing $N^\alpha$-acetyltransferase gene sequences. Techniques of nucleic acid hybridization are disclosed by Maniatis, T. et al., *In: Molecular Cloning, a Laboratory Manual*, Cold Spring Harbor, N.Y. (1982), and by Hames, B. D. and Higgins, S. J., *In: Nucleic Acid Hybrization, a Practical Approach*, IRL Press, Washington, D.C. (1985), which references are herein incorporated by reference. The source of DNA or cDNA used will preferably have been enriched for $N^\alpha$-acetyltransferase sequences. Such enrichment can most easily be obtained from cDNA obtained by extracting RNA from cells cultured under conditions which are characterized by $N^\alpha$-acetyltransferase expression.

Techniques such as, or similar to, those described above have successfully enabled the cloning of genes for human aldehyde dehydrogenases (Hsu, L. C. et al., *Proc. Natl. Acad. Sci. USA* 82:3771–3775 (1985)), fibronectin (Suzuki, S. et al., *Eur. Mol. Biol. Organ. J.* 4:2519–2524 (1985)), the human estrogen receptor gene (Walter, P. et al., *Proc Natl. Acad. Sci. USA* 82:7889–7893 (1985)), tissue-type plasminogen activator (Pennica, D. et al., *Nature* 301:214–221 (1983)) and human term placental alkaline phosphatase complementary DNA (Kam, W. et al., *Proc. Natl. Acad. Sci. USA* 82:8715–8719 (1985)).

In a preferred alternative way of cloning the $N^\alpha$-acetyltransferase gene, a library of expression vectors is prepared by cloning DNA or, more preferably cDNA, from a cell capable of expressing $N^\alpha$-acetyltransferase into an expression vector. The library is then screened for members capable of expressing a protein which binds to anti-$N^\alpha$-acetyltransferase antibody, and which has a nucleotide sequence that is capable of encoding polypeptides that have the same amino acid sequence as $N^\alpha$-acetyltransferase or fragments of $N^\alpha$-acetyltransferase.

The cloned $N^\alpha$-acetyltransferase gene, obtained through the methods described above, may be operably linked to an expression vector, and introduced into bacterial, or eukaryotic cells to produce $N^\alpha$-acetyltransferase protein. Techniques for such manipulations are disclosed by Maniatis, T. et al., supra, and are well known in the art.

The DNA sequence coding for $N^\alpha$-acetyltransferase may be derived from a variety of sources. For example, mRNA encoded for $N^\alpha$-acetyltransferase may be isolated from the tissues of any species that produces the enzyme, by using the Northern blot method (Alwine et al., *Method. Enzymol.* 68:220–242 (1979)), and labeled oligonucleotide probes. The mRNA may then be converted to cDNA by techniques known to those skilled in the art.

The DNA probe may be labeled with a detectable group. Such detectable group can be any material having a detectable physical or chemical property. Such materials have been well-developed in the field of immunoassays and in general most any label useful in such methods can be applied to the present invention. Particularly useful are enzymatically active groups, such as enzymes (see *Clin. Chem.* 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134,792); fluorescers (see *Clin. Chem.* 25:353 (1979)); chromophores; luminescers such as chemiluminescers and bioluminescers (see *Clin. Chem.* 25:512 (1979)); specifically bindable ligands; proximal interacting pairs; and radioisotopes such as $^3H$, $^{35}S$, $^{32}P$, $^{125}I$ and $^{14}C$. Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled probe can be detected by adding the enzyme for which the label is a cofactor and a substrate for the enzyme. For example, one can use an enzyme which acts upon a substrate to generate a product with a measurable physical property. Examples of the latter include, but are not limited to, beta-galactosidase, alkaline phosphatase and peroxidase.

C. Amino Acid Sequence Variants of the $N^\alpha$-Acetyltransferase

Amino acid sequence variants of the $N^\alpha$-acetyltransferase can be prepared by introducing mutations into the cloned $N^\alpha$-acetyltransferase cDNA sequence. Such variants include, for example, deletions from, or insertions or substitutions of, residues within the amino acid sequence encoded by the $N^\alpha$-acetyltransferase gene. Any combination of deletion, insertion, and substitution may be made. Obviously, unless null mutants are desired, the mutations that will be made in the DNA encoding the variant must not place the sequence out of reading frame and preferably will not create complementary regions that could produce secondary mRNA structure (see EP Patent Application Publication No. 75,444).

At the genetic level, these variants ordinarily are prepared by site-directed mutagenesis of nucleotides in the DNA encoding the $N^\alpha$-acetyltransferase, thereby producing DNA encoding the variant, and thereafter expressing the DNA in recombinant cell culture.

While the site for introducing an amino acid sequence variation may be determined in advance, the mutation per se need not be predetermined. For example, to optimize the performance of a mutation at a given site, random mutagenesis may be conducted at the target codon or region and the expressed $N^\alpha$-acetyltransferase variants screened for the optimal combination of desired activity. Techniques for making substitution mutations at predetermined sites in DNA having a known sequence are well known, for example, site-specific mutagenesis.

Preparation of a $N^\alpha$-acetyltransferase variant in accordance herewith is preferably achieved by site-specific mutagenesis of DNA that encodes an earlier prepared variant or a nonvariant version of the protein. Site-specific mutagenesis allows the production of $N^\alpha$-acetyltransferase variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing, J. et al., *3rd Cleveland Symp. Macromolecules Recombinant DNA*. Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and are typically (though not necessarily) contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete $N^\alpha$-acetyltransferase encoding sequence) may range generally from about 1 to 10 residues, more preferably 1 to 5. An example of a terminal insertion includes a fusion of a signal sequence, whether heterologous or homologous to the host cell, to the N-terminus of the $N^\alpha$-acetyltransferase to facilitate the secretion of mature $N^\alpha$-acetyltransferase from recombinant hosts.

The third group of variants are those in which at least one amino acid residue in the $N^\alpha$-acetyltransferase, and preferably, only one, has been removed and a different residue inserted in its place. Such substitutions preferably are made in accordance with the following Table 1 when it is desired to modulate finely the characteristics of the $N^\alpha$-acetyltransferase.

TABLE 1

| AMINO ACID SUBSTITUTIONS | |
|---|---|
| Original Residue | Exemplary Substitutions |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce such effects are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native $N^\alpha$-acetyltransferase-encoding nucleic acid, expression of the variant nucleic acid in recombinant cell culture, and, optionally, purification from the cell culture, for example, by immunoaffinity adsorption on a polyclonal anti-$N^\alpha$-acetyltransferase column (to absorb the variant by binding it to at least one remaining immune epitope).

The activity of the cell lysate or purified $N^\alpha$-acetyltransferase variant is then screened in a suitable screening assay for the desired characteristic. For example, a change in the immunological character of the altered $N^\alpha$-acetyltransferase, such as affinity for a given antibody, is measured by a competitive type immunoassay. Modifications of such protein properties as redox or thermal stability, hydrophobicity, susceptibility to proteolytic degradation or the tendency to aggregate with carriers or into multimers are assayed by methods well known to the ordinarily skilled artisan.

In order to identify variant $N^\alpha$-acetyltransferases which lack substantial $N^\alpha$-acetyltransferase activity, clones of the normal (i.e. active) $N^\alpha$-acetyltransferase may be mutagenized, and introduced into a null mutant. Since the majority of transformants will then exhibit $N^\alpha$-acetyltransferase activity, clones lacking $N^\alpha$-acetyltransferase activity can be readily identified.

In an analogous manner, it is possible to identify clones having enhanced or altered $N^\alpha$-acetyltransferase activity. Clones of a null allele (having a 1–10 amino acid substitution or deletion) may be mutagenized and introduced into a cell which is deficient in $N^\alpha$-acetyltransferase activity (such as a null mutant). Clones which, due to the mutagenesis have received a "correcting" or "compensating" mutation will, upon introduction into the cell, express $N^\alpha$-acetyltransferase activity. This activity can be assayed (in the manner described above) and the desired altered variants obtained.

D. Expression of the $N^\alpha$-acetyltransferase Gene Sequences

DNA or cDNA molecules which encode the $N^\alpha$-acetyltransferase enzyme of the present invention can be operably linked into an expression vector and introduced into a host cell to enable the expression of the $N^\alpha$-acetyltransferase enzyme by that cell. Two DNA sequences (such as a promoter region sequence and a desired enzyme encoding sequence) are said to be operably linked if the nature of the linkage between the two DNA sequences does not (1) result in the introduction of a frame-shift mutation, (2) interfere with the ability of the promoter region sequence to direct the transcription of the desired enzyme encoding gene sequence, or (3) interfere with the ability of the desired enzyme gene sequence to be transcribed by the promoter region sequence.

A DNA sequence encoding $N^\alpha$-acetyltransferase may be recombined with vector DNA in accordance with conventional techniques, including blunt-ended or stagger-ended termini for ligation, restriction enzyme digestion to provide appropriate termini, filling in of cohesive ends as appropriate, alkaline phosphatase treatment to avoid undesirable joining, and ligation with appropriate ligases.

The present invention encompasses the expression of the desired enzyme in any prokaryotic or eukaryotic cell.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for complement an auxotrophy in the host (such as leu2. or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

The $N^\alpha$-acetyltransferase of the invention may be isolated and purified in accordance with conventional conditions, such as extraction, precipitation, chromatography, affinity chromatography, electrophoresis, or the like.

1. Expression in Prokaryotic Cells

Preferred prokaryotic hosts include bacteria such as *E. coli, Bacillus, Streptomyces, Pseudomonas, Salmonella, Serratia*, etc. The most preferred prokaryotic host is *E. coli*. Bacterial hosts of particular interest include *E. coli* K12 strain 294 (ATCC 31446), *E. coli* X1776 (ATCC 31537), *E. coli* W3110 (F lambda prototrophic (ATCC 27325)), and other enterobacterium such as *Salmonella typhimurium* or *Serratia marcescens*, and various Pseudomonas species. The prokaryotic host must be compatible with the replicon and control sequences in the expression plasmid.

To express the desired enzyme in a prokaryotic cell (such as, for example, *E. coli, B. subtilis,* Pseudomonas, Streptomyces, etc.), it is necessary to operably link the desired enzyme encoding sequence to a functional prokaryotic promoter. Such promoters may be either constitutive or, more preferably, regulatable (i.e., inducible or derepressible). Examples of constitutive promoters include the int promoter of bacteriophage λ, and the bla promoter of the β-lactamase gene of pBR322, etc. Examples of inducible prokaryotic promoters include the major right and left promoters of bacteriophage λ ($P_L$ and $P_R$), the trp, recA, lacZ, lacI, gal, and tac promoters of *E. coli*, the α-amylase (Ulmanen, I., et al., *J. Bacteriol.* 162:176-182 (1985)) and the σ-28-specific promoters of B. subtilis (Gilman, M. Z., et al , *Gene* 32:11-20 (1984)), the promoters of the bacteriophages of Bacillus (Gryczan, T. J., In: *The Molecular Biology of the Bacilli,* Academic Press, Inc., N.Y. (1982)), and Streptomyces promoters (Ward, J. M., et al., *Mol Gen. Genet.* 203:468-478 (1986)). Prokaryotic promoters are reviewed by Glick, B. R., (*J. Ind. Microbiol.* 1:277-282 (1987)); Cenatiempo, Y. (*Biochimie* 68:505-516 (1986)); and Gottesman, S. (*Ann. Rev. Genet.* 18:415-442 (1984)).

Proper expression in a prokaryotic cell also requires the presence of a ribosome binding site upstream of the gene-encoding sequence. Such ribosome binding sites are disclosed, for example, by Gold, L., et al. (*Ann. Rev. Microbiol.* 35:365-404 (1981)).

The desired enzyme encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired enzyme may occur through the transient expression of the introduced sequence. Alternatively, permanent expression may occur through the integration of the introduced sequence into the host chromosome.

Preferred prokaryotic vectors include plasmids such as those capable of replication in *E. coli* (such as, for example, pBR322, ColE1, pSC101, pACYC 184, πVX. Such plasmids are, for example, disclosed by Maniatis, T., et al. (In: *Molecular Cloning, A Laboratory Manual,* Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli,* Academic Press, N.Y. (1982), pp. 307-329). Suitable Streptomyces plasmids include pIJ101 (Kendall, K. J., et al., *J. Bacteriol.* 169:4177-4183 (1987)), and streptomyces bacteriophages such as φC31 (Chater, K. F., et al., In: *Sixth International Symposium on Actinomycetales Biology,* Akademiai Kaido, Budapest, Hungary (1986), pp. 45-54) Pseudomonas plasmids are reviewed by John, J. F., et al. (*Rev. Infect. Dis.* 8:693-704 (1986)), and Izaki, K. (*Jpn. J. Bacteriol.* 33:729-742 (1978)).

Once the vector or DNA sequence containing the constructs has been prepared for expression, the DNA constructs may be introduced to an appropriate host. Various techniques may be employed, such as protoplast fusion, calcium phosphate precipitation, electroporation or other conventional techniques After the fusion, the cells are grown in media and screened for appropriate activities. Expression of the sequence results in the production of the substrate-specific aminopeptidase.

2. Expression in Eukaryotic Cells

Preferred eukaryotic hosts include yeast, fungi (especially Aspergillus), mammalian cells (such as, for example, human or primate cells) and plant cells either in vivo, or in tissue culture.

The expression of the desired enzyme in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, D., et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature (London)* 290:304-310 (1981)); the yeast gal4 gene promoter (Johnston, S. A., et al., *Proc. Natl. Acad. Sci. (USA)* 79:6971-6975 (1982); Silver, P. A., et al., *Proc. Natl. Acad Sci. (USA)* 81:5951-5955 (1984)).

As is widely known, translation of eukaryotic mRNA is initiated at the codon which encodes the first methionine. For this reason, it is preferable to ensure that the linkage between a eukaryotic promoter and a DNA sequence which encodes the desired enzyme (or a functional derivative thereof) does not contain any intervening codons which are capable of encoding a methionine (i.e., AUG). The presence of such codons results either in a formation of a fusion protein (if the AUG codon is in the same reading frame as the desired enzyme encoding DNA sequence) or a frame-shift mutation (if the AUG codon is not in the same reading frame as the desired enzyme encoding sequence).

a. Expression in Yeast

Yeast are the preferred hosts of the present invention. The use of yeast provides substantial advantages in that yeast can also carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

Any of a series of yeast gene expression systems can be utilized. Examples of such expression vectors include the yeast 2-micron circle, the expression plasmids YEP13, YCP and YRP, etc., or their derivatives. Such plasmids are well known in the art (Botstein, D., et al., *Miami Wntr. Symp.* 19:265-274 (1982); Broach, J. R., In: *The Molecular Biology of the Yeast Saccharomyces: Life Cycle and Inheritance*, Cold Spring Harbor Laboratory, Cold Spring Harbor, N.Y., p. 445-470 (1981); Broach, J. R., *Cell* 28:203-204 (1982)). YEP13 is the preferred vector of the present invention.

b. Expression in Mammalian Cells

Mammalian cells provide post-translational modifications to protein molecules including correct folding or glycosylation at correct sites. Mammalian cells which may be useful as hosts include cells of fibroblast origin such as VERO or CHO-K1, and their derivatives. For a mammalian host, several possible vector systems are available for the expression of the desired enzyme. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others.

c. Expression in Plant Cells

The $N^\alpha$-acetyltransferase of the present invention can be introduced into a plant by genetic engineering techniques to enhance the rate of acetylation. It is known that certain herbicides are inactivated by acetylation. Therefore, it is possible to produce a plant that is more herbicide-tolerant. In thus another embodiment of this invention, the $N^\alpha$-acetyltransferase gene is used to transform a plant to enhance the herbicidal tolerance of the plant.

The coding region for a $N^\alpha$-acetyltransferase gene that may be used in this invention may be homologous or heterologous to the plant cell or plant being transformed. It is necessary, however, that the genetic sequence coding for $N^\alpha$-acetyltransferase be expressed, and produced, as a functional protein or polypeptide in the resulting plant cell. Thus, the invention comprises plants containing either homologous $N^\alpha$-acetyltransferase genes or heterologous $N^\alpha$-acetyltransferase genes that express the enzyme.

In one embodiment of this invention, the $N^\alpha$-acetyltransferase comprises a plant $N^\alpha$-acetyltransferase that is homologous to the plant to be transformed. In another embodiment of this invention, the $N^\alpha$-acetyltransferase comprises an enzyme that is heterologous to the plant to be transformed. Moreover, DNA from both genomic DNA and cDNA encoding a $N^\alpha$-acetyltransferase gene may be used in this invention. Further, a $N^\alpha$-acetyltransferase gene may be constructed partially of a cDNA clone and partially of a genomic clone. In addition, the DNA coding for the $N^\alpha$-acetyltransferase gene may comprise portions from various species.

There are a variety of embodiments encompassed in the broad concept of the invention. In one of its embodiments, this invention comprises chimeric genetic sequences:

(a) a first genetic sequence coding for a $N^\alpha$-acetyltransferase that upon expression of the gene in a given plant cell is functional for $N^\alpha$-acetyltransferase;

(b) one or more additional genetic sequences operably linked on either side of the $N^\alpha$-acetyltransferase coding region. These additional genetic sequences contain sequences for promoter(s) or terminator(s). The plant regulatory sequences may be heterologous or homologous to the host cell.

In a preferred embodiment, the promoter of the $N^\alpha$-acetyltransferase gene is used to express the chimeric genetic sequence. Other promoters that may be used in the genetic sequence include nos, ocs, and CaMV promoters. An efficient plant promoter that may be used is an over-producing plant promoter. This promoter in operable linkage with the genetic sequence for $N^\alpha$-acetyltransferase should be capable of promoting expression of said $N^\alpha$-acetyltransferase such that the transformed plant has increased tolerance to a herbicide. Overproducing plant promoters that may be used in this invention include the promoter of the small subunit (ss) of the ribulose-1,5-biphosphate carboxylase from soybean (Berry-Lowe et al., *J. Molecular and App. Gen.*, 1:483-498 (1982)), and the promoter of the chlorophyll a/b binding protein. These two promoters are known to be light induced in eukaryotic plant cells (see, for example, *Genetic Engineering of Plants, an Agricultural Perspective*, A. Cashmore, Plenum, New York 1983, pages 29-38; Corruzi, G. et al., *J. of Biol. Chem.*, 258: 1399 (1983); and Dunsmuir, P. et al., *J. of Mol. and Applied Genet.*, 2: 285 (1983)).

Further, in another preferred embodiment, the expression of the chimeric genetic sequence comprising the $N^\alpha$-acetyltransferase gene is operably linked in correct reading frame with a plant promoter and with a gene secretion signal sequence.

The chimeric genetic sequence comprising a $N^\alpha$-acetyltransferase gene operably linked to a plant promoter, and in the preferred embodiment with the secretion signal sequences, can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells, typically resistance to antibiotics. The transforming vectors can be selected by these phenotypic markers after transformation in a host cell.

Host cells that may be used in this invention include prokaryotes, including bacterial hosts such as *E. coli, S. typhimurium,* and *Serratia marcescens.* Eukaryotic hosts such as yeast or filamentous fungi may also be used in this invention.

The cloning vector and host cell transformed with the vector are used in this invention typically to increase the copy number of the vector. With an increased copy number, the vectors containing the $N^\alpha$-acetyltransferase gene can be isolated and, for example, used to introduce the chimeric genetic sequences into the plant cells. The genetic material contained in the vector can be microinjected directly into plant cells by use of micropipettes to mechanically transfer the recombinant DNA. The genetic material may also be transferred into the plant cell by using polyethylene glycol which forms a precipitation complex with the genetic material that is taken up by the cell. (Paszkowski et al., *EMBO J.* 3:2717-22 (1984)).

In an alternative embodiment of this invention, the $N^\alpha$-acetyltransferase gene may be introduced into the plant cells by electroporation. (Fromm et al., "Expression of Genes Transferred into Monocot and Dicot Plant Cells by Electroporation," *Proc. Nat'l. Acad. Sci. U.S.A.* 82:5824 (1985)). In this technique, plant protoplasts are electroporated in the presence of plasmids containing the $N^\alpha$-acetyltransferase genetic construct. Electrical impulses of high field strength reversibly permeabilize biomembranes allowing the introduction of the plasmids. Electroporated plant protoplasts reform the cell wall, divide, and form plant callus. Selection of the transformed plant cells with the expressed $N^\alpha$-acetyltransferase can be accomplished using the phenotypic markers as described above.

Another method of introducing the $N^\alpha$-acetyltransferase gene into plant cells is to infect a plant cell with *Agrobacterium tumefaciens* transformed with the $N^\alpha$-acetyltransferase gene. Under appropriate conditions known in the art, the transformed plant cells are grown to form shoots, roots, and develop further into plants. The $N^\alpha$-acetyltransferase genetic sequences can be introduced into appropriate plant cells, for example, by means of the Ti plasmid of *Agrobacterium tumefaciens.* The Ti plasmid is transmitted to plant cells on infection by *Agrobacterium tumefaciens* and is stably integrated into the plant genome. (Horsch et al., "Inheritance of Functional Foreign Genes in Plants," *Science* 233:496-498 (1984); Fraley et al., *Proc. Nat'l Acad. Sci. U.S.A.* 80:4803 (1983)).

Ti plasmids contain two regions essential for the production of transformed cells. One of these, named transfer DNA (T DNA), induces tumor formation. The other, termed virulent region, is essential for the formation but not maintenance of tumors. The transfer DNA region, which transfers to the plant genome, can be increased in size by the insertion of the enzyme's genetic sequence without its transferring ability being affected. By removing the tumor-causing genes so that they no longer interfere, the modified Ti plasmid can then be used as a vector for the transfer of the gene constructs of the invention into an appropriate plant cell.

All plant cells which can be transformed by Agrobacterium and whole plants regenerated from the transformed cells can also be transformed according to the invention so to produce transformed whole plants which contain the transferred $N^\alpha$-acetyltransferase gene.

There are presently two different ways to transform plant cells with Agrobacterium:

(1) co-cultivation of Agrobacterium with cultured isolated protoplasts, or (2) transforming cells or tissues with Agrobacterium.

Method (1) requires an established culture system that allows culturing protoplasts and plant regeneration from cultured protoplasts.

Method (2) requires (a) that the plant cells or tissues can be transformed by Agrobacterium and (b) that the transformed cells or tissues can be induced to regenerate into whole plants. In the binary system, to have infection, two plasmids are needed: a T-DNA containing plasmid and a vir plasmid.

After transformation of the plant cell or plant, those plant cells or plants transformed by the Ti plasmid so that the enzyme is expressed, can be selected by an appropriate phenotypic marker. These phenotypical markers include, but are not limited to, antibiotic resistance. Other phenotypic markers are known in the art and may be used in this invention.

All plants from which protoplasts can be isolated and cultured to give whole regenerated plants can be transformed by the present invention so that whole plants are recovered which contain the transferred $N^\alpha$-acetyltransferase gene. Some suitable plants include, for example, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Zea, Triticum, Sorghum, and Datura.

There is an increasing body of evidence that practically all plants can be regenerated from cultured cells or tissues, including but not limited to all major cereal crop species, sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Monocotyledonous plants, and in particular, cereals and grasses, are not natural hosts to Agrobacterium. Attempts to transform them using Agrobacterium have been unsuccessful until recently. (Hooykas-Van Slogteren et al., *Nature* 311:763-764 (1984).) There is growing evidence now that certain monocots can be transformed by Agrobacterium. Using novel experimental approaches that have now become available, cereal and grass species may be transformable.

Additional plant genera that may be transformed by Agrobacterium include Ipomoea, Passiflora, Cyclamen, Malus, Prunus, Rosa, Rubus, Populus, Santalum, Allium, Lilium, Narcissus, Ananas, Arachis, Phaseolus, and Pisum.

Plant regeneration from cultural protoplasts is described in Evans et al., "Protoplast Isolation and Culture," in *Handbook of Plant Cell Culture* 1:124-176 (MacMillan Publishing Co., New York, 1983); M. R. Davey "Recent Developments in the Culture and Regeneration of Plant Protoplasts," *Protoplasts, 1983—Lecture Proceedings*, pp. 19-29 (Birkhauser, Basel, 1983); P. J. Dale, "Protoplast Culture and Plant Regeneration of Cereals and other Recalcitrant Crops," in *Protoplasts 1983—Lecture Proceedings*, pp. 31-41 (Birkhauser, Basel, 1983); and H. Binding, "Regeneration of Plants," in *Plant Protoplasts*, pp. 21-37 (CRC Press, Boca Raton, 1985).

Regeneration varies from species to species of plants, but generally a suspension of transformed protoplasts containing multiple copies of the $N^\alpha$-acetyltransferase gene is first provided. Embryo formation can then be induced from the protoplast suspensions, to the stage of ripening and germination as natural embryos. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed to produce an inbred plant. The inbred plant produces seed containing the gene for the increased $N^\alpha$-acetyltransferase. These seeds can be grown to produce plants that have enhanced rate of acetylation.

The inbreds according to this invention can be used to develop herbicide tolerant hybrids. In this method, a herbicide tolerant inbred line is crossed with another inbred line to produce the hybrid.

Parts obtained from the regenerated plant, such as flowers, seeds, leaves, branches, fruit, and the like are covered by the invention provided that these parts comprise the herbicidal tolerant cells. Progeny and variants, and mutants of the regenerated plants are also included within the scope of this invention.

In diploid plants, typically one parent may be transformed by the $N^\alpha$-acetyltransferase genetic sequence and the other parent is the wild type. After crossing the parents, the first generation hybrids (F1) will show a distribution of $\frac{1}{2}$ $N^\alpha$-acetyltransferase/wild type: $\frac{1}{2}$ $N^\alpha$-acetyltransferase/wild type. These first generation hybrids (F1) are selfed to produce second generation hybrids (F2). The genetic distribution of the F2 hybrids are $\frac{1}{4}$ $N^\alpha$-acetyltransferase/$N^\alpha$-acetyltransferase:$\frac{1}{2}$ $N^\alpha$-acetyltransferase/wild type: $\frac{1}{4}$ wild type/wild type. The F2 hybrids with the genetic makeup of $N^\alpha$-acetyltransferase/$N^\alpha$-acetyltransferase are chosen as the herbicidal tolerant plants.

As used herein, variant describes phenotypic changes that are stable and heritable, including heritable variation that is sexually transmitted to progeny of plants, provided that the variant still comprises a herbicidal tolerant plant through enhanced rate of acetylation. Also, as used herein, mutant describes variation as a result of environmental conditions, such as radiation, or as a result of genetic variation in which a trait is transmitted meiotically according to well-established laws of inheritance. The mutant plant, however, must still exhibit a herbicidal tolerance through enhanced rate of acetylation as according to the invention.

E. Uses of the $N^\alpha$-Acetyltransferase of the Present Invention

As discussed above, the present invention provides a means for producing $N^\alpha$-acetyltransferase enzymes, and for introducing gene sequences which encode these enzymes into diverse hosts.

Cells which lack $N^\alpha$-acetyltransferase activity (i.e. which express an altered $N^\alpha$-acetyltransferase substantially lacking $N^\alpha$-acetyltransferase activity) are highly desirable in facilitating the determination of the amino acid sequence of proteins. As discussed above, the presence of $N^\alpha$-acetyl groups on the amino acids of proteins greatly encumbers efforts to determine the amino acid sequence of such molecules. Since a cell which lacks $N^\alpha$-acetyltransferase activity would not catalyze the transfer of acetyl groups to the amino terminus of proteins, a protein produced in such a cell could be readily sequenced. Thus, for example, a cell carrying a null mutation in its $N^\alpha$-acetyltransferase gene could be used to produce endogenous yeast proteins lacking $N^\alpha$-acetylation. Such cells, for example, may be used to express a recombinant protein or peptide lacking an acetyl group at the protein's (or peptide's) $\alpha$-amino group. Such proteins could be easily sequenced using known methods.

In a similar manner, such a null mutant cell could be used as a host for the production of heterologous proteins (i.e. proteins not naturally or normally produced by such a cell) in order to facilitate the elucidation of the amino acid sequence of such proteins.

The ability to produce mutant cells whose $N^\alpha$-acetyltransferase is more active, or produced at higher levels, than normal $N^\alpha$-acetyltransferase, is desirable when one wishes to produce proteins having increased $N^\alpha$-acetylation. As discussed above, such proteins are desirable in being more stable than non-acetylated proteins.

The ability to alter the $N^\alpha$-acetyltransferase activity to conform to a desired activity (such as increased or decreased substrate specificity, thermal stability, etc.) is useful in permitting the development of host cells capable of producing proteins having altered $N^\alpha$-acetylation characteristics.

The altered $N^\alpha$-acetyltransferase enzymes can be purified and used in vitro in the same manner as described above for the mutant host cells.

Having now generally described this invention, the same will be better understood by reference to specific examples, which are included herein for purposes of illustration only, and are not intended to be limiting unless otherwise specified.

EXAMPLE 1

Purification of Methionine-Specific $N^\alpha$-Acetyltransferase From *S. Cerevisiae* (Strain T3A-A)

A culture (10×1 liter) of yeast (*S. cerevisiae* (strain t3a-a) was grown at 30° C., 200 rpm in YPD medium to $A_{600}$=6.0. Yeast crude lysates were prepared, and $N^\alpha$-acetyltransferase activity using proteinase A inhibitor 3 (1-24) as substrate was determined as previously described. These procedures, and that used to assay for enzyme activity were performed as described by Lee et al. (Lee, F-J. S., et al., *J. Biol. Chem.* 263:14948 (1988); Kamitani, K., et al., *J. Biol. Chem.* 264:13188 (1989), which references are incorporated herein by reference).

N-Ethylmaleimide (NEM), iodoacetic acid (IAA), iodoacetamide (IAM), dimethyl-(2-hydroxy-5-nitrobenzyl)sulfonium bromide ($HNBS(CH_3)_2$-Br), N-acetylimidazole, p-chloromercuribenzoate (pCMB), N-bromosuccinimide (NBS), diethyl pyrocarbonate (DEPC), HEPES, MES, CHES, DTT, hydroxylamine, bovine serum albumin, protein standards for $M_r$ determinations, 2-mercaptoethanol, glucose, sorbitol, lyticase, Bis-Tris, Tris and glycerol (enzyme grade) were from Sigma. DEAES-Sepharose CL-6B, Mono P (HR5/5), Polybuffer 96, Sepharose CL-6B were from Pharmacia. DE-52 cellulose and CM-52 cellulose were from Whatman. Protein assay reagent (Bradford method), hydroxylapatite (Biogel HT), Affi-Gel Blue gel and SDS-PAGE electrophoresis reagents were from Bio-Rad. [$^3$H] Acetyl coenzyme A was from Amersham, and unlabeled acetyl coenzyme A was from P-L Biochemicals. Reagents and solvents for amino acid analysis and Ready-Solv EP scintillation cocktails were obtained from Beckman. SP membrane was from Cuno Inc. PM-30 membrane was from Amicon. Yeast extract and Bacto-peptone were from Difco. Constant boiling (6N) HCl and Polybrene were from Pierce. Phenol was from BRL. Microdialyzer was from Health Products. Reagents and solvents for protein sequence analysis were from Applied Biosystems. Reagents for peptide synthesis were obtained from Applied Biosystems, and solvents for peptide synthesis were from Anachem. Boc-amino acids were from Peninsula. All other chemicals were reagent grade or better.

UV measurements were obtained using a Hewlett-Packard 8450A UV spectrophotometer. Protein assays were performed by the method of Bradford [Bradford, M. M., *Anal. Biochem.* 72:248–254 (1976)] using bovine serum albumin as the standard. Radioactive samples were counted on a Beckman LS 3801scintillation counter.

$N^\alpha$-acetyltransferase activity was determined as previously described [Lee et al., *J. Biol. Chem.* 263:14948–14955 (1988)]. Aliquots of the lysate or chromatographic fractions were added to 1.5 ml Eppendorf tubes containing a reaction mixture of 50 mM HEPES, pH 7.4, 150 mM KCl, 1 mM DTT, 25 $\mu$M [$^3$H] acetyl coenzyme A (0.5 $\mu$Ci) and 50 $\mu$M synthetic peptide with an adjusted final volume of 100 $\mu$l. The assay mixture was incubated at 30° C. for 30 min. The reaction was stopped by adding 17 $\mu$l of 0.5M acetic acid and chilled in an ice bath. The reaction samples were filtered through SP membrane discs (Cuno) (previously pre-swollen in 0.5M acetic acid), and then washed three times with 1 ml of 0.5M acetic acid on a Millipore 1225 sampling manifold. The partially dried membranes were placed in scintillation cocktail and counted with a Beckman LS 3801 scintillation counter. One unit of activity was defined as the amount of enzyme able to transfer 1 pmol of [$^3$H] acetyl group from [$^3$H] acetyl coenzyme A to synthetic peptide per min under standard enzyme assay conditions defined above.

The supernatant solution of crude lysates was concentrated to a volume of 10 ml, using a PM-30 ultrafiltration membrane and dialyzed overnight against 2×2 liters of HDG buffer (20 mM HEPES, pH 7.4, 0.5 mM DDT, 10% (v/v) glycerol and 0.02% $NaN_3$) containing 0.2M KCl. The dialyzed supernatant fluid was applied to DEAE Sepharose CL-6B (2.5×55 cm) equilibrated with HDG buffer containing 0.2M KCl and eluted with the same buffer. The fractions (4 ml each) containing enzyme activity were pooled, concentrated to a volume of 5 ml, dialyzed overnight against 2×2 liters of HDG buffer containing 0.05M KCl, and then applied to a DE-52 cellulose column (2.5×55 cm) equilibrated in HDG buffer containing 0.05M KCl. The column was eluted with a linear gradient of 0.05M (250 ml) to 0.5M (250 ml) KCl in HDG buffer. Fractions (3.5 ml each) containing enzyme activity were pooled, concentrated to a volume of 2.5 ml, dialyzed overnight against 2×2 liters of HDG buffer (20 mM MES, pH 6.7, 0.5 mM DDT, 10% (v/v) glycerol and 0.02% $NaN_3$) containing 0.05M KCl, and then applied to a CM-52 cellulose column 2.5×50 cm) equilibrated in MDG buffer containing 0.05M KCl. The column was eluted with a linear gradient of 0.05M (250 ml) to 0.5M (250 ml) KCl in MDG buffer. Fractions (3.0 ml each) were collected, and the fractions containing enzyme activity (at about 0.15M KCl) were pooled, concentrated to a volume of 1.0 ml, and applied to a Sepharose CL-6B column (2.0×90 cm) equilibrated with 0.1M potassium phosphate buffer, pH 7.4, 0.5 mM DDT, 10% (v/v) glycerol, 0.02% $NaN_3$. The column was eluted with the same buffer. Fractions (3.5 ml each) containing enzyme activity were pooled, concentrated to a volume of 0.5 ml, and applied to a hydroxylapatite (Bio-Rad) column (2.0×15 cm) equilibrated with 0.1M potassium phosphate buffer, pH 7.4, 0.5 mM DDT, 10% (v/v) glycerol, 0.02% NaN$_3$. The column was eluted with a linear gradient of 0.1M (100 ml) to 0.6M (100 ml) potassium phosphate buffer, pH 7.4, containing 0.5 mM DDT, 10% (v/v) glycerol, 0.02% NaN$_3$. Fractions (2.0 ml each) were collected, and the fractions containing enzyme activity (at about 0.45M KH$_2$PO$_4$) were pooled and concentrated to a volume of 0.5 ml. Protein was determined by the Bradford assay (Bio-Rad) (33) with bovine serum albumin as the standard.

The results of the above-described purification are shown in Table 2 below.

TABLE 2

Purification of methionine N$^\alpha$-Acetyltransferase from S. cerevisiae

| Step | Activity (units) | Protein (mg) | Specific Activity (unit/mg) | Purification (fold) | Yield (%) |
|---|---|---|---|---|---|
| 1. Crude Extract | 6400 | 2200 | 2.9 | 1.0 | 100 |
| 2. DEAE-Sepharose | 3760 | 410 | 9.2 | 3.2 | 59 |
| 3. DE52-cellulose | 2450 | 110 | 22.3 | 7.7 | 38[a] |
| 4. CM52-cellulose | 1400 | 2.2 | 636 | 219 | 22 |
| 5. Affi-Gel Blue gel | 940 | 0.8 | 1180 | 407 | 15 |
| 6. Hydroxylapatite | 380 | 0.04 | 9500 | 3280 | 6 |

[a]An apparent inhibitor was removed during this chromatographic step.

EXAMPLE 2

Purification of Methionine-Specific N$^\alpha$-Acetyltransferase From S. Cerevisiae (Strain TD 71.8)

Methionine specific N$^\alpha$-acetyltransferase was also purified to apparent homogeneity from S. cerevisiae strain TD 71.8. Enzyme activity was determined as described in Example 1. 1000 liters of yeast culture (TD 71.8) was grown aerobically at 30° C. in YPD medium (1% yeast extract, 2% Bacto-peptone, 2% glucose) in a Chemap AG fermentor (Chemap AG, Volketswil, Switzerland). Cells were harvested when the culture reached an OD$_{660\,nm}$ of 14, concentrated to 24 liters by Alfa-Laval separation system (Alfa-Laval Separation AB, Tumba, Sweden), and stored at −20° C. with 10% (v/v) glycerol for up to 4 months without loss of activity.

Cell Extraction. Concentrated yeast culture (4 liters) was thawed and collected by centrifugation at 4000 rpm for 20 min (JS-4.0 rotor, Beckman). The cells (600 g, wet weight) were resuspended in 750 ml of buffer A (50 mM Tris-HCl, pH 7.8, 10 mM MgCl$_2$, 3 mM DTT, 1M sorbitol) containing 60 mg of lyticase, and the cell suspension was shaken gently at 30° C. for 45 min. All subsequent steps were carried out at 4° C. The spheroplasts were collected by centrifugation at 4000 rpm for 15 min (JS-4.0 rotor, Beckman), washed by gentle resuspension in 500 ml of buffer A, collected by centrifugation and resuspended gently in 360 ml of buffer B (10 mM HEPES, pH 7.4, 1.5 mM MgCl$_2$, 10 mM KCl, and 0.5 mM DTT). The spheroplasts were lysed in this hypotonic buffer by fifteen strokes with a tight-fitting pestle and fifteen strokes with a loose-fitting pestle in a Dounce homogenizer, and then cold KCl (2.0M) was added to give a final KCl concentration of 0.2M. The homogenate was gently shaken for 45 min, and debris was removed by centrifugation at 14,000 rpm for 45 min (JA 14 rotor, Beckman) The supernatant solution was concentrated to a volume of 60 ml, using a PM-30 ultrafiltration membrane and dialyzed overnight against 2×4 liters of HDG (20 mM HEPES, pH 7.4, 0.5 mM DTT, 10% (v/v) glycerol and 0.02% NaN$_3$) buffer containing 0.2M KCl.

DEAE-Sepharose CL-6B Chromatography. DEAE Sepharose CL-6B was prepared, degassed, and packed into a column (2.5×55 cm) following the manufacturer's recommendations. The column was washed with 4 column volumes of HDG buffer containing 0.2M KCl. The dialyzed supernatant fluid was applied to DEAE Sepharose CL-6B equilibrated with HDG buffer containing 0.2M KCl. Methionine acetyltransferase activity was eluted with same buffer at 24 ml/h. Fractions (5 ml) were collected, and the fractions containing methionine acetyltransferase activity were pooled and concentrated to a volume of 30 ml, using a PM-30 ultrafiltration membrane.

DE-52 Cellulose Chromatography. The concentrated eluate from the DEAE Sepharose CL-6B chromatography was dialyzed overnight against 2×4 liters of HDG buffer containing 0.05M KCl and then applied to a DE-52 cellulose column (2.5×55 cm) equilibrated in HDG buffer containing 0.05M KCl. The column was eluted with a linear gradient of 0.05M (250 ml) to 0.5M (250 ml) KCl in HDG buffer at 24 ml/h. Fractions (3.5 ml) were collected, and the fractions containing methionine acetyltransferase activity were pooled and concentrated to a volume of 15 ml, using a PM-30 ultrafiltration membrane.

CM-52 Cellulose Chromatography. The concentrated eluate from the DE-52 cellulose chromatography was dialyzed overnight against 2×4 liters of MDG (20 mM MES, pH 6.7, 0.5 mM DTT, 10% (v/v) glycerol and 0.02% NaN$_3$) buffer containing 0.1M KCl and then applied to a CM-52 cellulose column (2.5×55 cm) equilibrated in MDG buffer containing 0.1M KCl. The column was eluted with a linear gradient of 0.1M (250 ml) to 0.5M (250 ml) KCl in MDG buffer at 24 ml/h. Fractions (3.0 ml) were collected, analyzed for A$_{280}$, conductivity, and acetyltransferase activity, as described above, and the fractions containing methionine acetyltransferase activity were pooled and concentrated to a volume of 1.5 ml, using a PM-30 ultrafiltration membrane.

Affi-Gel Blue Gel Chromatography. The concentrated eluate from the CM-52 cellulose chromatography was dialyzed overnight against 4 liters of HDG buffer containing 0.05M KCl and applied to an Affi-Gel Blue gel column (1.5×20 cm) equilibrated in HDG buffer containing 0.05M KCl. The column was eluted with a linear gradient of 0.05M (110 ml) to 0.5M (110 ml) KCl in HDG buffer at 12 ml/h and analyzed for A$_{280}$, conductivity, and acetyltransferase activity, as described above, fractions having methionine acetyltransferase activity were pooled and concentrated to a volume of 0.5 ml, using a PM-30 ultrafiltration membrane.

Hydroxylapatite Chromatography. The concentrated eluate from the Affi-Gel Blue gel chromatography was dialyzed overnight against 2×2 liters of 0.2M potassium phosphate buffer, pH 7.2, 0.5 mM DTT, 10% (v/v) glycerol, 0.02% NaN$_3$ and applied to a hydroxylapatite column (2.0×15 cm) equilibrated with the same buffer used for dialysis. The column was eluted with a linear gradient of 0.1M (100 ml) to 0.8M (100 ml) potassium phosphate buffer, pH 7.2, containing 0.5 mM DTT, 10% (v/v) glycerol, 0.02% NaN₃ at 24 ml/h. Fractions (2.0 ml) were collected, analyzed for A₂₈₀, conductivity, and acetyltransferase activity, as described above, and the fractions containing methionine acetyltransferase activity were pooled and concentrated to a volume of 0.5 ml, using a PM-30 ultrafiltration membrane.

Sodium Dodecyl Sulfate-Polyacrylamide Gel Electrophoresis. A sample of hydroxylapatite pool containing methionine acetyltransferase, dialyzed against double-distilled water, was loaded on a SDS-PAGE gel (9%) and electrophoresed, under reducing conditions, as described by Laemmli (Laemmli, U.K., Nature 227:680-685 (1970)). For determination of $M_r$ of purified enzyme subunits, myosin (205,000), E. coli β-galactosidase (116,000), rabbit muscle phosphorylase (97,000), bovine serum albumin (66,000), egg albumin (45,000), and horse spleen carbonic anhydrase (29,000) were used as molecular weight standards. Protein bands were stained with Coomassie Brilliant Blue R. A single band of Mr 69,000±2,000 was observed.

Molecular Size Determination. The $M_r$ of the native methionine acetyltransferase was estimated by comparison to molecular weight standards by gel filtration on Sepharose CL-6B column (2.5×95 cm). Partially purified enzyme, purified through the Affi-Gel Blue gel chromatography, was applied to the column. The column was eluted with MDG buffer containing 0.1M KCl at 20 ml/h. The elution volume of the enzyme was determined by $A_{280}$nm and enzyme activity, and the apparent molecular weight of methionine acetyltransferase was calculated by comparison with the relative elution volumes of protein standards including thyroglobulin (669,000), apoferrin (443,000), β-amylase (200,000), alcohol dehydrogenase (150,000), bovine serum albumin (66,000) and carbonic anhydrase (29,000). The $M_r$ of the native enzyme was estimated to be 70,000±5,000.

Chromatofocusing on Mono P. Partially purified enzyme, purified through the Affi-Gel Blue gel chromatography, was applied to a Mono P (HR 5/5) column equilibrated with 75 mM Tris-acetic acid buffer (pH 9.3) and eluted with Polybuffer 96 (pH 6) at the flow rate of 1 ml/min at 4° C. Elution was monitored by A₂₈₀ nm, and 0.5 ml fractions were collected for measurement of pH and enzyme activity.

As shown in Table 3, the multiple step purification from 600 g yeast cells resulted in a 22,000-fold purification. The enzyme consisted of approximately 0.001% of total cellular protein. SDS-PAGE revealed a single Coomassie blue stained band with an $M_r$=69,000±2,000. Gel filtration chromatography on Sepharose CL-6B showed that the $M_r$ of the native M-N$^α$AT is 70,000±5,000. These data indicated that the yeast methionine specific N$^α$-acetyltransferase is monomeric. Chromatofocusing on Mono P revealed a single peak at apparent pI=8.3.

The effect of temperature and pH on yeast methionine acetyltransferase was investigated. The specific activity of yeast acetyltransferase for PAI was determined at different temperatures as described above. The specific activity of yeast acetyltransferase for PAI was determined in 50 mM buffers of potassium phosphate, HEPES, CHES, and CAPS buffers of different pH's as described above. Assays for determining the temperature optimum for M-N$^α$-acetyltransferase were performed from 5° to 55° C., and the enzyme displayed a maximum activity at temperatures from 25° to 37° C. Irreversible denaturation occurred after 1 min at 60° C.

The enzyme was most stable when stored at 4° C. in MDG buffer (20 mM MES, pH 6.7, 0.5 mM DTT, 10% (v/v) glycerol and 0.02% NaN₃) containing 0.1M KCl. Under these conditions the half-life of the purified enzyme was approximately 14 days. The enzyme displayed an approximate 25% loss of activity per freeze-thaw cycle. The pH dependence of the yeast M-N$^α$-acetyltransferase was measured by assaying at pH values from 5 to 10 in the presence of 50 mM of either potassium phosphate, HEPES, CHES, or MES buffers. Maximum enzyme activity was observed at pH 7. Enzyme activity was <25% below pH 5 and above pH 9. The presence of KCl or NaCl up to 0.5M did not affect the enzyme activity, although a 50% reduction in enzyme activity was observed when the enzyme assay was performed at 0.8M KCl or NaCl.

TABLE 3

Purification of methionine N$^α$-Acetyltransferase from S. cerevisiae

| Step | Activity (units) | Protein (mg) | Specific Activity (unit/mg) | Purification (fold) | Yield (%) |
|---|---|---|---|---|---|
| 1. Crude Extract | 26900 | 14200 | 1.9 | 1.0 | 100 |
| 2. DEAE-Sepharose | 27500 | 3100 | 8.9 | 4.7 | 102 |
| 3. DE52-cellulose | 53200 | 830 | 64 | 33.7 | 198[a] |
| 4. CM52-cellulose | 16800 | 12.3 | 1370 | 720 | 62 |
| 5. Affi-Gel Blue gel | 6240 | 0.65 | 9600 | 5050 | 23 |
| 6. Hydroxylapatite | 2100 | 0.05 | 42000 | 22000 | 8 |

[a]An apparent inhibitor was removed during this chromatographic step.

EXAMPLE 3

Characterization of the N$^α$-Acetyltransferase

Since the peptide substrates used previously in the enzyme assay for the AAA1 encoded N$^α$-acetyltransferase contained either serine or alanine as amino-terminal residues (Lee, F-J. S., et al., J. Biol. Chem. 263:14948 (1988); Kamitani, K., et al., J. Biol. Chem. 264:13188 (1989)), these peptide substrates were used in the present invention to assay crude lysates from the aaa1 mutant and wild-type yeast strains (Table 4).

Table 4 shows the N$^α$-acetylation of various peptide substrates by crude yeast lysates from wild-type and aaa1 mutant strains. The wild-type (containing endogenous N$^α$-acetyltransferase activity) and the aaa1 (lacking endogenous N$^α$-acetyltransferase activity) strains were T3A and T3A-a, respectively (Lee, F-J. S., et al., J. Bacteriol. 171, 5795-5802 (1989)). Human adrenocorticotropic hormone (1-24), yeast alcohol dehydrogenase (1-24), and human superoxide dismutase (1-24) have either serine or alanine as amino-terminal residues, while proteinase A inhibitor 3 has a methionine residue. The synthesis of the peptide substrates, the preparation of the crude yeast homogenate, and the assay of enzyme activity were as previously described by Lee et al. (Lee, F-J. S., et al., J. Biol. Chem. 263:14948 (1988); Kamitani, K., et al., J. Biol. Chem. 264:13188 (1989)). The numbers in parentheses refer to the residue numbers, and the letters in parentheses specify the amino acid sequence. Abbreviations: A (alanine), C (cysteine), D (aspartic acid), E (glutamic acid), F (phenylalanine), G (glycine), H (histidine), I (isoleucine), K (lysine), L (leucine), M (methionine), N (asparagine), P (proline), Q (glutamine), R (arginine), S (serine), T (threonine), V (valine), W (tryptophan). Data are reported as mean activity±SD (N=3-5) and are normalized to the activity of the homogenate towards human adrenocorticotropic hormone (1-24).

Although it was expected that only one $N^\alpha$-acetyltransferase would be responsible for transferring an acetyl group to the α-amino group of proteins capable of being $N^\alpha$-acetylated (Tsunasawa, S., et al., *Methods Enzymol.* 106:165 (1984); Driessen, H. P. C., et al., *CRC Crit. Rev. Biochem.* 18:281 (1985); Wold, F., *Trends Biochem. Sci.* 9:256 (1984); Jornvall, H., *J. Theoret. Biol.* 55:1 (1975); Rubenstein, P. et al., *J. Biol. Chem.* 254:11142 (1979)), the presence of a methionine $N^\alpha$-acetyltransferase was assayed for, since it was assumed that if there were additional $N^\alpha$-acetyltransferases then one specific for methionine might exist (FIG. 1).

Using a peptide substrate that mimicked the amino-terminus of the only yeast protein in the SwissProt protein sequence database known to contain an $N^\alpha$-acetylated methionine residue, proteinase A inhibitor 3 (Biederman, K., et al., *Carlsberg Res. Commun.* 45:225 (1980)), it was observed that both the aaa1 mutant and the wild-type strains were capable of acetylating this substrate, although, as expected, the aaa1 mutant was incapable of acetylating the peptide substrates containing serine or alanine as amino terminal residues (Table 4). These data demonstrate difinitively that a methionine $N^\alpha$-acetyltransferase exists in yeast cells.

45:225-235 (1980)). Therefore, a series of peptide substrates mimicking various iso-1-cytochrome c mutant proteins (previously established to be $N^\alpha$-acetylated or to contain a free α-amino group (Tsunasawa, J. W., et al., *J. Biol. Chem.* 260:5382 (1985)), as well as actin, were synthesized (Table 5). Table 5 shows the $N^\alpha$-acetylation of various amino-terminal methionine containing peptide substrates by a crude yeast homogenate from the aaa1 mutant strain (lacking endogenous $N^\alpha$-acetyltransferase activity), T3A-a (Lee, F-J. S., et al., *J. Bacteriol.* 171:5795-5802 (1989)). The synthesis of the peptide substrates, the preparation of the crude yeast homogenate, and the assay of enzyme activity were as previously described by Lee et al. (Lee, F-J. S., et al., *J. Biol. Chem.* 263:14948 (1988); Kamitani, K., et al., *J. Biol. Chem.* 264:13188 (1989)). The numbers in parentheses refer to the residue numbers, and the letters in parentheses refer to the amino acid sequence Abbreviations are as in FIG. 1. Data are reported as mean activity ±SD (N=3-5) and are normalized to the activity of the homogenate towards yeast proteinase A inhibitor 3. The sequence of this protein is:

M-N-T-D-Q-Q-K-V-S-E-I-F-Q-S-S-K-E-K-L-Q-G-D-A-K

Each substrate contained an amino-terminal methionine and asparagine, aspartic acid, alanine, leucine, or threonine, as the penultimate residues $N^\alpha$-Acetylation

TABLE 4

| $N^\alpha$-ACETYLATION OF VARIOUS PEPTIDE SUBSTRATES | | |
|---|---|---|
| | Activity (%) | |
| Peptide | AAA1 | aaa1 |
| Adrenocorticotropic hormone (1-24) (Human) (S-Y-S-M-E-H-F-R-W-G-K-P-V-G-K-K-R-R-P-V-K-V-Y-P) | 100 ± 5 | 0 |
| Alcohol dehydrogenase (1-24) (Yeast) (S-I-P-E-T-Q-K-G-V-I-F-Y-E-S-H-G-K-L-E-Y-K-D-I-P) | 102 ± 5 | 0 |
| Superoxide dismutase (1-24) (Human) (A-T-K-A-V-C-V-L-K-G-D-G-P-V-Q-G-S-I-N-F-E-Q-K-E) | 80 ± 6 | 0 |
| Proteinase A Inhibitor 3 (1-24) (Yeast) (M-N-T-D-Q-Q-K-V-S-E-I-F-Q-S-S-K-E-K-L-Q-G-D-A-K) | 75 ± 5 | 80 ± 5 |

EXAMPLE 4

Specificity of the $N^\alpha$-Acetyltransferase

From an analysis of eukaryotic protein sequences, Jornvall and coworkers previously demonstrated that five amino acid residues (i.e., alanine, serine, methionine, glycine, and threonine) account for 95% of all acetylated residues in eukaryotic proteins and that $N^\alpha$-acetylated methionine is invariably followed by aspartic acid, glutamic acid or asparagine (Perrson, B., et al., *Eur. J. Biochem.* 152:523 (1985)).

Proteinase A inhibitor 3 (PAI) (Tsunasawa et al., *Methods Enzymol.* 106:165-170 (1984); Wold, F., *Trends Biochem. Sci.* 9:256-267 (1984); Driessen et al., *CRC Crit. Rev. Biochem* 18:281-325 (1985); Mullen et al., *EMBO J.* 8:2067-2075 (1989); Lee et al., *J. Bacteriol.* 171:5795-5802 (1989); Hershko et al., *Proc. Natl. Acad. Sci. USA* 81:7021-7025 (1984); Bachmair et al., *Science* 234:179-186 (1986); Arfin et al., *Biochemistry* 27:7979-7984 (1988); Persson et al., *Eur. J. Biochem.* 152:523-527 (1985); Huang al., *Biochemistry* 26:8242-8246 (1987); Lee et al., *J. Biol. Chem.* 263:14948-14955 (1988); Kamitani et al., *J. Biol. Chem.* 264:13188-13193 (1989)) is the only known yeast protein which is acetylated at its NH2-terminal methionine residue (Biedermann et al., *Carlsberg Res. Commun.* of methionine was found to occur only for substrates containing asparagine or aspartic acid as the penultimate residue. Data is reported as mean activity ±SD (N=3-5).

TABLE 5

| RELATIVE ACTIVITY OF YEAST METHIONINE ACETYLTRANSFERASE FOR THE $N^\alpha$-ACETYLATION OF SYNTHETIC PEPTIDES | |
|---|---|
| Substrate | Activity (%)[a] |
| PROTEINASE A INHIBITOR 3 (1-24) (Yeast) | 100 ± 5 |
| [Ala2]PROTEINASE A INHIBITOR 3 (1-24) (Yeast) | 0 |
| [Arg2]PROTEINASE A INHIBITOR 3 (1-24) (Yeast) | 0 |
| [Asp2]PROTEINASE A INHIBITOR 3 (1-24) (Yeast) | 55 ± 5 |
| [Cys2]PROTEINASE A INHIBITOR 3 (1-24) (Yeast) | 0 |
| [Gln2]PROTEINASE A INHIBITOR 3 (1-24) (Yeast) | 9 ± 3 |
| [Glu2]PROTEINASE A INHIBITOR 3 (1-24) (Yeast) | 21 ± 3 |
| [Gly2]PROTEINASE A INHIBITOR 3 (1-24) (Yeast) | 0 |
| [Ile2]PROTEINASE A INHIBITOR 3 (1-24) (Yeast) | 0 |
| [Leu2]PROTEINASE A INHIBITOR 3 (1-24) (Yeast) | 0 |

TABLE 5-continued

RELATIVE ACTIVITY OF YEAST METHIONINE ACETYLTRANSFERASE FOR THE $N^\alpha$-ACETYLATION OF SYNTHETIC PEPTIDES

| Substrate | Activity (%)$^a$ |
|---|---|
| [His$_2$]PROTEINASE A INHIBITOR 3 (1-24) (Yeast) | 0 |
| [Lys$_2$]PROTEINASE A INHIBITOR 3 (1-24) (Yeast) | 0 |
| [Met$_2$]PROTEINASE A INHIBITOR 3 (1-24) (Yeast) | 0 |
| [Phe$_2$]PROTEINASE A INHIBITOR 3 (1-24) (Yeast) | 0 |
| [Pro$_2$]PROTEINASE A INHIBITOR 3 (1-24) (Yeast) | 0 |
| [Ser$_2$]PROTEINASE A INHIBITOR 3 (1-24) (Yeast) | 0 |
| [Thr$_2$]PROTEINASE A INHIBITOR 3 (1-24) (Yeast) | 0 |
| [Trp$_2$]PROTEINASE A INHIBITOR 3 (1-24) (Yeast) | 0 |
| [Tyr$_2$]PROTEINASE A INHIBITOR 3 (1-24) (Yeast) | 0 |
| [Val$_2$]PROTEINASE A INHIBITOR 3 (1-24) (Yeast) | 0 |

Thus, by using PAI, its analogues and other peptides, the structural features of M-N$^\alpha$AT substrates were studied. Nineteen synthetic PAI analogues with substitution at penultimate position were compared to PAI, which was previously demonstrated to be effectively N$^\alpha$-acetylated (Lee et al., *J. Biol. Chem.* 265:3603–3606 (1990)) (Table 5). Only three of nineteen analogues were acetylated, although the efficiency of their acetylation varied from 9–55% (Asp>Glu>Gln). Although it was shown previously that iso-cytochrome c variant proteins (Met-Ile-Arg - - -, Met-Ile-Lys - - -, Met-Met-Asn - - -) can be N$^\alpha$-acetylated in vivo (Tsunasawa et al., *J. Biol. Chem.* 260:5382–5391 (1985)), synthetic peptides mimicking the NH$_2$-terminal 24 amino acid residues of these iso-cytochrome c variants were not acetylated by the yeast M-N$^\alpha$AT.

EXAMPLE 5

Comparative Specificity of N$^\alpha$-Acetyltransferases

In order to compare the relative specificity and activity of the methionine N$^\alpha$-acetyltransferase activity (M-N$^\alpha$-AT) of the present invention with the specificity and activity of the AAA1 N$^\alpha$-acetyltransferase (N$^\alpha$-AT) of Lee, F.-J. S., et al., *J. Bacteriol.* 171, (1989), U.S. Patent Application of John A. Smith, and Fang-Jen S. Lee, filed Oct. 25, 1989, entitled "ISOLATION OF STRAINS OF *SACCHAROMYCES CEREVISIAE* HAVING ALTERED N$^\alpha$-ACETYLTRANSFERASE ACTIVITY" (which references have been incorporated herein by reference) synthetic peptides were prepared. These peptides were assessed for their ability to serve as substrates for the two enzymes. The results of this experiment are shown in Tables 6 and 7. In Table 6, the effect of the amino terminal amino acid on activity is investigated; in Table 7, the effect of the penultimate amino terminal amino acid on activity is investigated.

TABLE 6

RELATIVE ACTIVITY OF YEAST ACETYLTRANSFERASES N$^a$-AT AND M-N$^a$-AT FOR THE N$^a$-ACETYLATION OF SYNTHETIC PEPTIDES: INFLUENCE OF THE AMINO TERMINAL RESIDUE

| Substrate | Activity (%) (mean activity ± S.D.) N$^a$-AT M-N$^a$-AT |
|---|---|
| ACTH (Human)<br>S-Y-S-M-E-H-F-R-W-G-K-P-V-G-K-K-R-R-P-V-K-V-Y-P | 100 ± 500 |
| ALCOHOL DEHYDROGENASE I (1-24) (Yeast)<br>S-I-P-E-T-Q-K-G-V-I-F-Y-E-S-H-G-K-L-E-Y-K-D-I-P | 102 ± 50 |
| [A'] ALCOHOL DEHYDROGENASE I (1-24) (Yeast)<br>A-I-P-E-T-Q-K-G-V-I-F-Y-E-S-H-G-K-L-E-Y-K-D-I-P | 00 |
| [R'] ALCOHOL DEHYDROGENASE I (1-24) (Yeast)<br>R-I-P-E-T-Q-K-G-V-I-F-Y-E-S-H-G-K-L-E-Y-K-D-I-P | 00 |
| [N'] ALCOHOL DEHYDROGENASE I (1-24) (Yeast)<br>N-I-P-E-T-Q-K-G-V-I-F-Y-E-S-H-G-K-L-E-Y-K-D-I-P | 00 |
| [D'] ALCOHOL DEHYDROGENASE I (1-24) (Yeast)<br>D-I-P-E-T-Q-K-G-V-I-F-Y-E-S-H-G-K-L-E-Y-K-D-I-P | 00 |
| [C'] ALCOHOL DEHYDROGENASE I (1-24) (Yeast)<br>C-I-P-E-T-Q-K-G-V-I-F-Y-E-S-H-G-K-L-E-Y-K-D-I-P | 00 |
| [Q'] ALCOHOL DEHYDROGENASE I (1-24) (Yeast)<br>Q-I-P-E-T-Q-K-G-V-I-F-Y-E-S-H-G-K-L-E-Y-K-D-I-P | 00 |
| [E'] ALCOHOL DEHYDROGENASE I (1-24) (Yeast)<br>E-I-P-E-T-Q-K-G-V-I-F-Y-E-S-H-G-K-L-E-Y-K-D-I-P | 00 |
| [G'] ALCOHOL DEHYDROGENASE I (1-24) (Yeast)<br>G-I-P-E-T-Q-K-G-V-I-F-Y-E-S-H-G-K-L-E-Y-K-D-I-P | 23 ± 30 |
| [I'] ALCOHOL DEHYDROGENASE I (1-24) (Yeast)<br>I-I-P-E-T-Q-K-G-V-I-F-Y-E-S-H-G-K-L-E-Y-K-D-I-P | 00 |
| [L'] ALCOHOL DEHYDROGENASE I (1-24) (Yeast)<br>L-I-P-E-T-Q-K-G-V-I-F-Y-E-S-H-G-K-L-E-Y-K-D-I-P | 00 |
| [H'] ALCOHOL DEHYDROGENASE I (1-24) (Yeast)<br>H-I-P-E-T-Q-K-G-V-I-F-Y-E-S-H-G-K-L-E-Y-K-D-I-P | 19 ± 20 |
| [K'] ALCOHOL DEHYDROGENASE I (1-24) (Yeast)<br>K-I-P-E-T-Q-K-G-V-I-F-Y-E-S-H-G-K-L-E-Y-K-D-I-P | 00 |
| [M'] ALCOHOL DEHYDROGENASE I (1-24) (Yeast)<br>M-I-P-E-T-Q-K-G-V-I-F-Y-E-S-H-G-K-L-E-Y-K-D-I-P | 15 ± 20 |
| [F'] ALCOHOL DEHYDROGENASE I (1-24) (Yeast)<br>F-I-P-E-T-Q-K-G-V-I-F-Y-E-S-H-G-K-L-E-Y-K-D-I-P | 9 ± 20 |
| [P'] ALCOHOL DEHYDROGENASE I (1-24) (Yeast)<br>P-I-P-E-T-Q-K-G-V-I-F-Y-E-S-H-G-K-L-E-Y-K-D-I-P | 70 ± 40 |
| [T'] ALCOHOL DEHYDROGENASE I (1-24) (Yeast)<br>T-I-P-E-T-Q-K-G-V-I-F-Y-E-S-H-G-K-L-E-Y-K-D-I-P | 103 ± 50 |
| [W'] ALCOHOL DEHYDROGENASE I (1-24) (Yeast)<br>W-I-P-E-T-Q-K-G-V-I-F-Y-E-S-H-G-K-L-E-Y-K-D-I-P | 00 |

TABLE 6-continued

RELATIVE ACTIVITY OF YEAST ACETYLTRANSFERASES $N^a$-AT AND M-$N^a$-AT FOR THE $N^a$-ACETYLATION OF SYNTHETIC PEPTIDES: INFLUENCE OF THE AMINO TERMINAL RESIDUE

| Substrate | Activity (%) (mean activity ± S.D.) $N^a$-ATM-$N^a$-AT |
|---|---|
| [Y'] ALCOHOL DEHYDROGENASE I (1-24) (Yeast)<br>Y-I-P-E-T-Q-K-G-V-I-F-Y-E-S-H-G-K-L-E-Y-K-D-I-P | 20 ± 20 |
| [V'] ALCOHOL DEHYDROGENASE I (1-24) (Yeast)<br>V-I-P-E-T-Q-K-G-V-I-F-Y-E-S-H-G-K-L-E-Y-K-D-I-P | 69 ± 40 |

TABLE 7

RELATIVE ACTIVITY OF YEAST ACETYLTRANSFERASES $N^a$-AT AND M-$N^a$-AT FOR THE $N^a$-ACETYLATION OF SYNTHETIC PEPTIDES: INFLUENCE OF THE PENULTIMATE AMINO TERMINAL RESIDUE

| Substrate | Activity (%) (mean activity ± S.D.) | |
|---|---|---|
| | $N^a$-AT | M-$N^a$-AT |
| ACTH (Human)<br>S-Y-S-M-E-H-F-R-W-G-K-P-V-G-K-K-R-R-P-V-K-V-Y-P | 100 ± 5 | 0 |
| ALCOHOL DEHYDROGENASE I (1-24) (Yeast)<br>S-I-P-E-T-Q-K-G-V-I-F-Y-E-S-H-G-K-L-E-Y-K-D-I-P | 102 ± 5 | 0 |
| [$A^2$] ALCOHOL DEHYDROGENASE I (1-24) (Yeast)<br>S-A-P-E-T-Q-K-G-V-I-F-Y-E-S-H-G-K-L-E-Y-K-D-I-P | 168 ± 8 | 0 |
| [$R^2$] ALCOHOL DEHYDROGENASE I (1-24) (Yeast)<br>S-R-P-E-T-Q-K-G-V-I-F-Y-E-S-H-G-K-L-E-Y-K-D-I-P | 102 ± 5 | 0 |
| [$N^2$] ALCOHOL DEHYDROGENASE I (1-24) (Yeast)<br>S-N-P-E-T-Q-K-G-V-I-F-Y-E-S-H-G-K-L-E-Y-K-D-I-P | 116 ± 5 | 0 |
| [$D^2$] ALCOHOL DEHYDROGENASE I (1-24) (Yeast)<br>S-D-P-E-T-Q-K-G-V-I-F-Y-E-S-H-G-K-L-E-Y-K-D-I-P | 171 ± 9 | 0 |
| [$C^2$] ALCOHOL DEHYDROGENASE I (1-24) (Yeast)<br>S-C-P-E-T-Q-K-G-V-I-F-Y-E-S-H-G-K-L-E-Y-K-D-I-P | 136 ± 7 | 0 |
| [$Q^2$] ALCOHOL DEHYDROGENASE I (1-24) (Yeast)<br>S-Q-P-E-T-Q-K-G-V-I-F-Y-E-S-H-G-K-L-E-Y-K-D-I-P | 134 ± 7 | 0 |
| [$E^2$] ALCOHOL DEHYDROGENASE I (1-24) (Yeast)<br>S-E-P-E-T-Q-K-G-V-I-F-Y-E-S-H-G-K-L-E-Y-K-D-I-P | 121 ± 6 | 0 |
| [$G^2$] ALCOHOL DEHYDROGENASE I (1-24) (Yeast)<br>S-G-P-E-T-Q-K-G-V-I-F-Y-E-S-H-G-K-L-E-Y-K-D-I-P | 84 ± 5 | 0 |
| [$L^2$] ALCOHOL DEHYDROGENASE I (1-24) (Yeast)<br>S-L-P-E-T-Q-K-G-V-I-F-Y-E-S-H-G-K-L-E-Y-K-D-I-P | 126 ± 5 | 0 |
| [$H^2$] ALCOHOL DEHYDROGENASE I (1-24) (Yeast)<br>S-H-P-E-T-Q-K-G-V-I-F-Y-E-S-H-G-K-L-E-Y-K-D-I-P | 125 ± 6 | 0 |
| [$K^2$] ALCOHOL DEHYDROGENASE I (1-24) (Yeast)<br>S-K-P-E-T-Q-K-G-V-I-F-Y-E-S-H-G-K-L-E-Y-K-D-I-P | 151 ± 6 | 0 |
| [$M^2$] ALCOHOL DEHYDROGENASE I (1-24) (Yeast)<br>S-M-P-E-T-Q-K-G-V-I-F-Y-E-S-H-G-K-L-E-Y-K-D-I-P | 140 ± 7 | 0 |
| [$F^2$] ALCOHOL DEHYDROGENASE I (1-24) (Yeast)<br>S-F-P-E-T-Q-K-G-V-I-F-Y-E-S-H-G-K-L-E-Y-K-D-I-P | 118 ± 6 | 0 |
| [$P^2$] ALCOHOL DEHYDROGENASE I (1-24) (Yeast)<br>S-P-P-E-T-Q-K-G-V-I-F-Y-E-S-H-G-K-L-E-Y-K-D-I-P | 0 | 0 |
| [$S^2$] ALCOHOL DEHYDROGENASE I (1-24) (Yeast)<br>S-S-P-E-T-Q-K-G-V-I-F-Y-E-S-H-G-K-L-E-Y-K-D-I-P | 140 ± 6 | 0 |
| [$T^2$] ALCOHOL DEHYDROGENASE I (1-24) (Yeast)<br>S-T-P-E-T-Q-K-G-V-I-F-Y-E-S-H-G-K-L-E-Y-K-D-I-P | 144 ± 8 | 0 |
| [$W^2$] ALCOHOL DEHYDROGENASE I (1-24) (Yeast)<br>S-W-P-E-T-Q-K-G-V-I-F-Y-E-S-H-G-K-L-E-Y-K-D-I-P | 91 ± 5 | 0 |
| [$Y^2$] ALCOHOL DEHYDROGENASE I (1-24) (Yeast)<br>S-Y-P-E-T-Q-K-G-V-I-F-Y-E-S-H-G-K-L-E-Y-K-D-I-P | 169 ± 8 | 0 |
| [$V^2$] ALCOHOL DEHYDROGENASE I (1-24) (Yeast)<br>S-V-P-E-T-Q-K-G-V-I-F-Y-E-S-H-G-K-L-E-Y-K-D-I-P | 123 ± 7 | 0 |

EXAMPLE 6

Amino Acid Analysis of $N^a$-Acetyltransferase

The concentrated eluate from the Affi-Gel Blue gel chromatography was applied to a 9% SDS-PAGE gel of 1.5 mm thickness in a 12 cm well, electrophoresed, and electroeluted as previously described (Hunkapiller et al., *Methods Enzymol.* 91:227-236 (1983)). Purified methionine $N^a$-acetyltransferase was electroeluted from the preparative SDS-PAGE gel. The amino acid composition was determined from four different enzyme preparations using a Beckman 6300 Amino Acid Analyzer after 24 h hydrolysis at 110° C. in 6N HCl containing 0.1% phenol (Hewick et al., *J. Biol. Chem.* 256:7990-7997 (1981); Moore, S., in *Chemistry and Biology of Peptides* (Meienhofer, J., ed.), Ann Arbor Science, Ann Arbor, Mich. (1972), p. 629-652). Asx=Asp+Asn; Glx=Glu+Gln. The residue number per subunit of enzyme was calculated on the basis of a $M_r$=69,000, and assuming a mass of 110 for each amino acid residue. No correction was made for the amounts of Ser and Thr destroyed during the 24 hr hydrolysis. Cys and Trp were not determined.

TABLE 8
AMINO ACID COMPOSITION OF METHIONINE $N^a$-ACETYLTRANSFERASE FROM S. CEREVISIAE

| Amino Acid | Observed Residues |
|---|---|
| Asx | 84 |
| Thr | 29 |
| Ser | 47 |
| Glx | 74 |
| Pro | 27 |
| Gly | 48 |
| Ala | 38 |
| Val | 44 |
| Met | 2 |
| Ile | 23 |
| Leu | 64 |
| Tyr | 11 |
| Phe | 31 |
| Lys | 54 |
| His | 16 |
| Arg | 32 |

EXAMPLE 7

Effect of Divalent Cations on Enzyme Activity

The effect of various divalent cations on the M-$N^a$AT activity was determined (Table 9). Yeast methionine acetyltransferase was incubated in the presence of various divalent cations at a room temperature for 5 min in 50 mM HEPES, pH 7.4 containing 1 mM DTT. The enzyme activity was determined under standard assay conditions using PAI (N=3), as described above. At 1 mM concentration, $Ca^{2+}$, $Mg^{2+}$ and $Mn^{2+}$ had no effect, whereas pronounced and concentration-dependent inhibition occurred in the presence of other divalent ions ($Zn^{2+} = Cu^{2+} = Cd^{2+} > Co^{2+} = Fe^{2+}$ partially inactivated enzyme at 0.1 mM. Further, it was demonstrated that the pronounced effects, observed with $CuSO_4$ and $ZnSO_4$, were not due to the $SO_4^{-2}$ anion, since $MgSO_4$ did not affect enzyme activity as compared with the activity in the presence of $MgCl_2$. In addition, the $CdCl_2$ inhibition was not due to $Cl^-$, since $CaCl_2$, $MgCl_2$, and $MnCl_2$ did not affect enzyme activity.

TABLE 9
EFFECT OF DIVALENT CATIONS ON ENZYME ACTIVITY OF METHIONINE $N^a$-ACETYLTRANSFERASE FROM S. CEREVISIAE

| | Enzyme Activity (%) Concentration (mM) | | |
|---|---|---|---|
| Salt added | 1 | 0.1 | 0.01 |
| None | 100 | — | — |
| $CaCl_2$ | 102 | — | — |
| $MgCl_2$ | 98 | 105 | — |
| $MgSO_4$ | 97 | 102 | — |
| $MnCl_2$ | 98 | 103 | — |
| $FeSO_4$ | 40 | 93 | 108 |
| $CoCl_2$ | 38 | 95 | 106 |
| $CdCl_2$ | 0 | 72 | 103 |
| $CuSO_4$ | 0 | 65 | 101 |
| $ZnSO_4$ | 0 | 52 | 95 |

EXAMPLE 8

Effect of Chemical Modifications on Enzyme Activity

In order to determine the possible catalytic role for different types of amino acid residues in the enzyme, various chemical modifications were carried out (Table 10). Yeast methionine acetyltransferase was incubated with each reagent at 30° C. for 15 min, dialyzed against 50 mM HEPES, pH 7.4, 150 mM, 1 mM DTT at 4° C. for 3 to 4 hr. The enzyme activity was determined under standard assay conditions using PAI (N=3), assayed as described above.

The abbreviations used are: α-MSH, α-melanocyte-stimulating hormone; CHES, 2-(N-cyclohexylamino)ethanesulfonic acid; DEPC, diethyl pyrocarbonate; HDG buffer, 20 mM HEPES, pH 7.4, 0.5 mM DTT, 10% (v/v) glycerol and 0.02% $NaN_3$; NBS, N-bromosuccinimide; $HNBS(CH_3)_2$-Br, dimethyl-(2-hydroxy-5-nitrobenzyl)sulfonium bromide; HEPES, N-2-hydroxyethylpiperazine-N'-2-ethanesulfonic acid; IAA, iodoacetic acid; IAM, iodoacetamide; MDG buffer, 20 mM MES, pH 6.7, 0.5 mM DTT, 10% (v/v) glycerol and 0.02% $NaN_3$; MES, 2-(N-morpholino) ethanesulfonic acid; M-$N^a$AT, methionine-$N^a$-acetyltransferase; $N^a$AT, $N^a$-acetyltransferase; NBS, N-bromosuccinimide; NEM, N-ethylmaleimide; PAI, proteinase A inhibitor 3; pCMB, p-chloromercuribenzoate; SDS-PAGE, sodium dodecyl sulfate-polyacrylamide gel electrophoresis.

The reaction of M-$N^a$AT with diethyl pyrocarbonate, a histidine-modifying reagent Miles, E. W., *Methods Enzymol.* 47:431-442 (1977)), caused a nearly complete inactivation of the enzyme. After incubation for 6 hr at room temperature with 0.25M hydroxylamine, a reagent capable of reversing the thoxyformylation of a histidine residue, ~50% of the original enzyme activity was recovered, although prolonged exposure to hydroxylamine slowly inactivated the enzyme. The presence of a catalytically important tryptophan residue was investigated by chemical modification with NBS (Spande et al., *Methods Enzymol.* 11:506-522 (1967)) and $HNBS(CH_3)_2$-Br (Horton et al., *Methods Enzymol.* 25:468-482 (1972)).

NBS partially inactivated the enzyme at 0.5 mM and completely inactivated the enzyme at 5 mM. Although HNBS $(CH_3)_2$-Br partially inactivated the enzyme, the loss of enzyme activity was smaller in comparison to NBS. Since NBS can also modify histidine and tyrosine residues (Witkop, B., *Adv. Protein Chem.* 16:221-321 (1963)), it is possible that the inactivation might be due to a chemical modification of the same histidine(s), presumably modified by DEPC. Sulfhydryl-reducing agents (i.e., 2-mercaptoethanol and DTT) did not affect the enzyme activity. Sulfhydryl-modifying reagents (i.e., iodoacetic acid, iodoacetamide, and pCMB) were also without effect at 1 mM, but partial inactivation of the enzyme was observed at 0.5 mM with NEM and at 10 mM with the other reagents. N-acetylimidazole, a tyrosine-modifying reagent, was also without effect Riordan et al., *Methods Enzymol.* 25:500-506 (1972)).

TABLE 10
EFFECT OF PROTEIN MODIFICATION REAGENTS ON ENZYME ACTIVITY OF METHIONINE $N^A$-ACETYLTRANSFERASE FROM S. CEREVISIAE

| Reagent Added[b] | Concentration (mM) | Enzyme Activity (%) |
|---|---|---|
| None | | 100.0 |
| DEPC | 0.05 | 59 |
| | 0.5 | 0 |
| NBS | 0.5 | 30 |
| | 5.0 | 0 |
| $HNBS(CH_3)_2$-Br | 1.0 | 93 |
| | 10.0 | 62 |
| 2-mercaptoethanol | 10.0 | 96 |
| DTT | 10.0 | 95 |
| NEM | 0.5 | 77 |
| | 5.0 | 20 |
| IAA | 1.0 | 102 |

TABLE 10-continued

EFFECT OF PROTEIN MODIFICATION REAGENTS ON ENZYME ACTIVITY OF METHIONINE $N^A$-ACETYLTRANSFERASE FROM S. CEREVISIAE

| Reagent Added[b] | Concentration (mM) | Enzyme Activity (%) |
|---|---|---|
| IAM | 10.0 | 75 |
| | 1.0 | 100 |
| pCMB | 10.0 | 86 |
| | 1.0 | 94 |
| N-acetylimidazole | 10.0 | 25 |
| | 1.0 | 100 |
| | 10.0 | 93 |

EXAMPLE 9

Mechanism of $N^\alpha$-Acetylation

The present invention illuminates the role for a methionine $N^\alpha$-acetyltransferase in protein synthesis. One possibility is that $N^\alpha$-acetylation of methionine-containing proteins (accounting for 5–6% of acetylated proteins (Perrson, B., et al., Eur. J. Biochem. 152:523 (1985)) is required to be highly specific to subserve important biological functions, although the reason why the $N^\alpha$-acetylation of all other proteins is apparently so non-specific is unclear.

Figure 2:
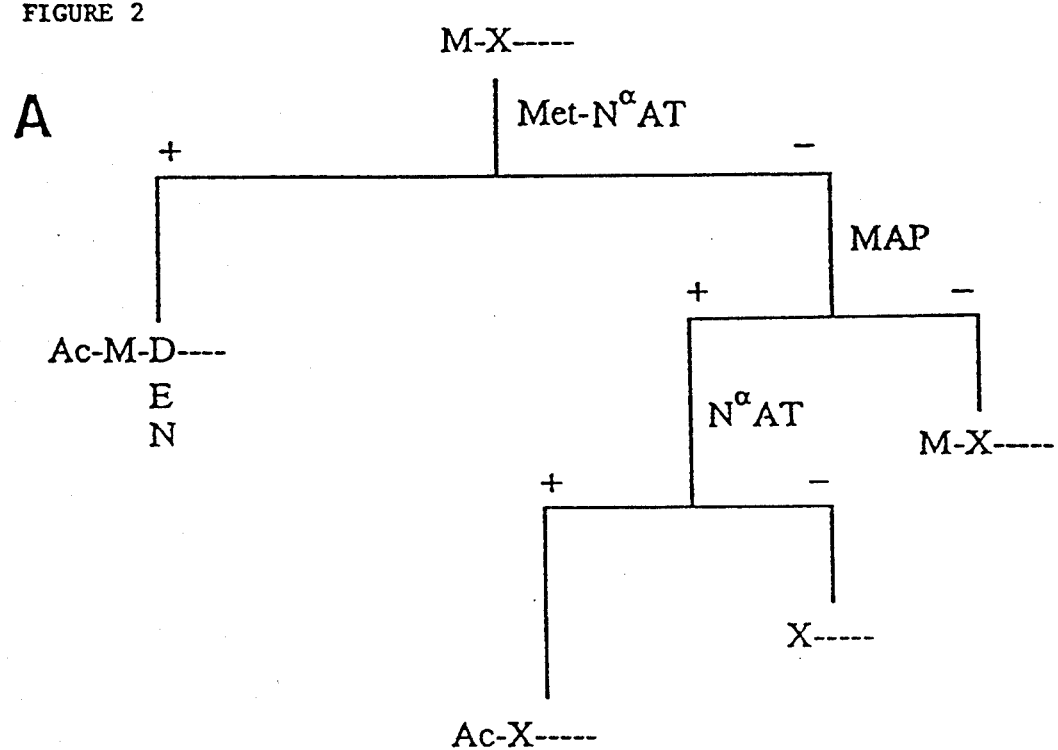
FIG. 2 shows (A) proposed pathway for the co-translational modification of eukaryotic proteins mediated by methionine $N^\alpha$-acetyltransferase (M—$N^\alpha$AT), methionine aminopeptidase (MAP), and $N^\alpha$-acetyltransferase ($N^\alpha$—AT), and (B) alternative pathway involving a single $N^\alpha$—AT acting at two different stages of acetylation and acyl-amino acid hydrolase (AAH).
Figure 2:
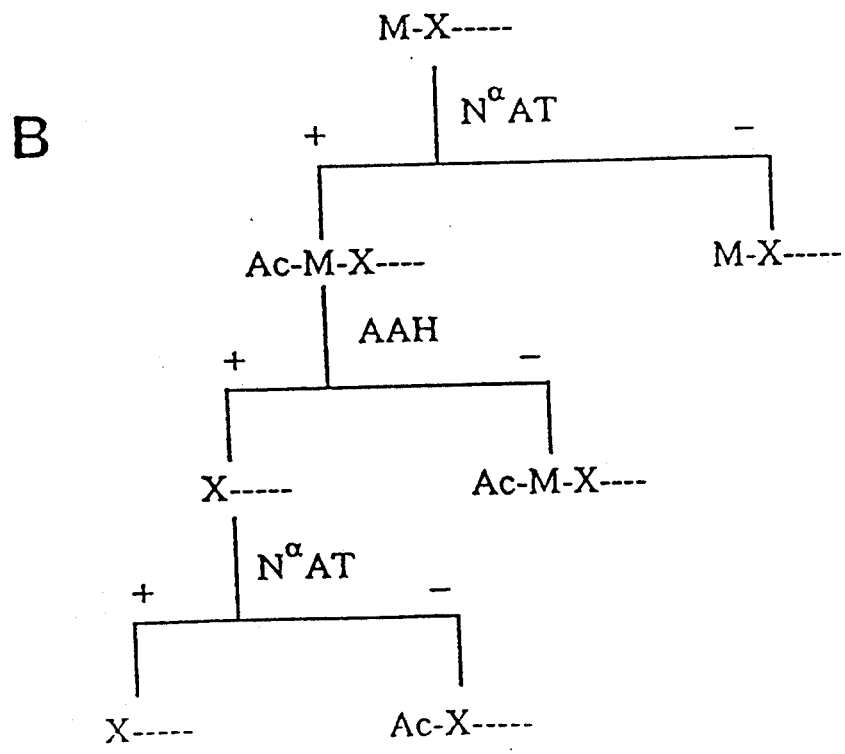

Another possibility is that acetylation of the proteins containing methionine occurs at a different stage of proteins synthesis from the acetylation of other poteins (FIGS. 2A and B). FIG. 2 shows (A) proposed pathway for the co-translational modification of eukaryotic proteins mediated by methionine $N^\alpha$-acetyltransferase (M-$N^\alpha$AT), methionine aminopeptidase (MAP), and $N^\alpha$-acetyltransferase ($N^\alpha$-AT), and (B) alternative pathway involving a single $N^\alpha$-AT acting at two different stages of acetylation and acyl-amino acid hydrolase (AAH), as previously proposed by Wold (Wold, F., Trends Biochem. Sci. 9:256 (1984)). This pathway does not require the action of MAP. The symbols are as indicated in FIG. 1. For example, if acetylation of the initiator methionine (FIG. 2A), not its cleavage by a methionine aminopeptidase (FIG. 1), is the first step in co-translational protein processing of certain proteins, then the substrate specificity of methionine $N^\alpha$-acetyltransferase might control which proteins would be cleaved by methionine aminopeptidase, and thereby which proteins would later be acetylated by another $N^\alpha$-acetyltransferase. Alternatively, methionine $N^\alpha$-acetyltransferase might function on proteins containing an amino-terminal methionine at the same stage of synthesis where the other $N^\alpha$-acetyltransferase functions (FIG. 1).

In summary, it is now clear that acetylation is neither mediated by a single $N^\alpha$-acetyltransferase affecting all possible amino-terminal residues (FIG. 1) nor by a single $N^\alpha$-acetyltransferase operating at two distinct stages of co-translational modification (Narita, K., Biochim. Biophys. Acta 28:184 (1958)), but rather that two distinct $N^\alpha$-acetyltransferases regulate $N^\alpha$-acetylation of eukaryotic proteins.

M-$N^\alpha$AT selectively transfers an acetyl group from acetyl-CoA to $NH_2$-terminal Met residues adjacent to Asp, Asn, Glu, or Gln. Yeast M-$N^\alpha$AT was purified 22,000-fold with an overall recovery of 8% by successive chromatographic procedures utilizing DEAE-Sepharose, DE52-cellulose, CM52-cellulose, Affi-Gel Blue gel, and hydroxylapatite (Table 3). The enzyme was $NH_2$-terminally blocked. The $M_r$ of the native enzyme was 70,000±5,000, and the enzyme was a monomer with a $M_r$ of 69,000±2,000 as revealed from SDS-PAGE. M-$N^\alpha$AT also differs from $N^\alpha$AT both in its $M_r$ (70,000 versus 200,000) and subunit structure (monomer versus dimer). In addition, M-$N^\alpha$AT and $N^\alpha$AT were inhibited markedly by $Cu^{2+}$ and $Zn^{2+}$, although M-$N^\alpha$AT but not $N^\alpha$AT was also inhibited by $Cd^{2+}$ (Table 8).

Furthermore, neither M-$N^\alpha$AT nor $N^\alpha$AT were activated by chloride ion, as previously demonstrated for the wheat germ $N^\alpha$AT (Kido et al., Arch. Biochem. Biophys. 208:95–100 (1981)).

Studies involving other acetyltransferases have shown that chemical modification of cysteine in acetyl-CoA:arylamine N-acetyltransferase (Jencks et al., J. Biol. Chem. 247:3756–3760 (1972)) and choline o-acetyltransferase (Roskoski, R., Jr., J. Biol. Chem. 249:2156–2159 (1974)) or of histidine in acetyl-CoA:α-glucosaminide N-acetyltransferase (Bame et al., J. Biol. Chem. 261:10127–10132 (1986)) inactivated these enzymes. The inability of β-mercaptoethanol, DTT, NEM, pCMB, IAA, and IAM to inactivate both enzyme indicates that a cysteine residue is probably not involved in the catalytic mechanism (Table 10). The studies using DEPC (and possibly NBS) suggest that a histidine residue may be located within the active site of yeast M-$N^\alpha$AT, as was previously suggested for yeast $N^\alpha$AT (Lee et al., J. Biol. Chem. 263:14948–14955 (1988)). Such a histidine residue has also been proposed to function as a general base in the catalytic site of chloramphenicol acetyltransferase (Leslie et al., Proc. Natl. Acad. Sci. USA 85:4133–4137 (1988)).

From an analysis of eukaryotic protein sequences, it was previously demonstrated that five amino acid residues (i.e., alanine, serine, methionine, glycine and threonine) account for 95% of all acetylated resides in eukaryotic proteins (Tsunasawa et al., Methods Enzymol. 106:165–170 (1984); Wold, F., Trends Biochem. Sci. 9:256–267 (1984); Driessen et al., CRC Crit. Rev. Biochem 18:281–325 (1985); Jornvall, H., J. Theoret. Biol. 55:1–12 (1975); Arfin et al., Biochemistry 27:7979–7984 (1988); Persson et al., Eur. J. Biochem. 152:523–527 (1985)). Although this predominant use of certain amino acid residues suggests that an $NH_2$-terminal residue is the primary recognition signal for $N^\alpha$-acetyltransferases, there are numerous examples of proteins having these amino acids as their $NH_2$-termini that are not acetylated. Thus, it is likely that the enzymes may also recognize adjacent residues (e.g., $N^\alpha$-acetylated methionine is usually followed by asparagine, aspartic acid, or glutamic acid), distal residues (Kamitani et al., J. Biol. Chem. 264:13188–13193 (1989); Lee et al., J. Biol. Chem. 265:3603–3606 (1990); Augen et al., Trends Biochem. Sci. 11:494–497 (1986); Dixon et al., Methods Enzymol. 106:170–179 (1984)) or conformational features within the $NH_2$-terminal region of a protein or peptide. Therefore, a series of synthetic peptide substrates was synthesized mimicking PAI known to be $N^\alpha$-acetylated at its $NH_2$-terminal methionine (Biedermann et al., Carlsberg Res. Commun. 45:225–235 (1980)), as well as iso-1 cytochrome c variants (previously established to be $N^\alpha$-acetylated in vivo (Tsunasawa et al., J. Biol. Chem. 260:5382–5391 (1985))). Each substrate set bore an $NH_2$-terminal methionine with various amino acids at the penultimate residue. It was found that $N^\alpha$-acetylation of methionine occurred only for substrates containing asparagine, aspartic acid, glutamic acid or glutamine, as the penultimate residue (Table 5). Furthermore, the differences in the relative activity for acetylation of the NH$_2$-terminal Met of PAI and its analogues indicated that the penultimate residue has a major role in controlling N$^\alpha$-acetylation by M-N$^\alpha$AT. Although a protein containing a N$^\alpha$-acetylated NH$_2$-terminal methionine followed by Gln has not been previously observed in various protein databases (Driessen et al., *CRC Crit. Rev. Biochem.* 18:281-325 (1985); Jornvall, H., *J. Theoret. Biol.* 55:1-12 (1975); Persson et al., *Eur. J. Biochem.* 152:523-527 (1985); Huang et al., *Biochemistry* 26:8242-8246 (1987)), this failure to identify such a protein may be due to the limited number of N$^\alpha$-acetylated proteins that have been characterized to date.

The fact that synthetic peptides of human protein-tyrosine-phosphatase can be acetylated by yeast M-N$^\alpha$AT (Lee et al., *J. Biol. Chem.* 265:3603-3606 (1990)) indicates that the substrate specificity of M-N$^\alpha$AT is likely to be highly conserved between yeast and human. Therefore, purified yeast M-N$^\alpha$AT may provide a ready source of enzyme for studying the catalytic mechanism and substrate specificity of both the yeast and human enzyme.

A biological function for the yeast N$^\alpha$AT in cell growth and mating was shown previously by disrupting its gene (AAA1; also called NATI (Mullen et al., *EMBO J.* 8:2067-2075 (1989); Lee et al., *J. Biol. Chem.* 264:12339. Because it was shown that the acetylated methionine is subsequently removed (presumably by either a N-acetylmethionine aminopeptidase (Radhakrishna et al., *J. Biol. Chem.* 261:9572-9575 (1986)) or an acylpeptide hydrolase (Tsunasawa et al., *J. Biochem. (Tokyo)* 77:89-102 (1975); Kobayashi et al., *J. Biol. Chem.* 262:11435-11445 (1987))), and because the penultimate residue is subsequently acetylated and the present demonstration that M-N$^\alpha$AT will acetylate a 24 residue synthetic peptide mimicking the NH$_2$ terminus of yeast actin (Lee et al., *J. Biol. Chem.* 265:3603-3606 (1990)), it is likely that selective acetylation of Met is important in the regulation of NH$_2$-terminal processing pathways of actin and other eukaryotic proteins.

Partial protein sequence data M-N$^\alpha$AT has been determined from tryptic peptides and is currently being utilized to clone the encoding gene. Later, while using yeast as a genetic analysis system, the cloned gene will form the basis for a direct investigation of the functional role of M-N$^\alpha$AT in protein N$^\alpha$-acetylation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A *Saccharomyces cerevisiae* methionine N$^\alpha$-acetyltransferase substantially pure and specific for N-terminal methionine residues.

2. The methionine N$^\alpha$-acetyltransferase of claim 1, wherein said methionine N$^\alpha$-acetyltransferase transfers an acetyl group from acetyl-CoA to a NH$_2$-terminal methionine residue that is adjacent to a member of the group consisting of aspartic acid, asparagine, glutamic acid and glutamine.

3. The methionine N$^\alpha$-acetyltransferase of claim 1, wherein said methionine N$^\alpha$-acetyltransferase is purified from yeast by a method comprising, in successive order:
  (a) DEAE-Sepharose chromatography;
  (b) DE52-cellulose chromatography;
  (c) CM52-cellulose chromatography;
  (d) Affi-Gel Blue gel chromatography; and
  (e) hydroxylapatite.

4. The methionine N$^\alpha$-acetyltransferase of claim 2, wherein said methionine N$^\alpha$-acetyltransferase is NH$_2$-terminally blocked.

5. The methionine N$^\alpha$-acetyltransferase of claim 2, wherein said methionine N$^\alpha$-acetyltransferase is a monomer of molecular weight 70,000±5,000 daltons.

6. The methionine N$^\alpha$-acetyltransferase of claim 2, wherein the enzymatic activity of said methionine N$^\alpha$-acetyltransferase is inhibited by cadmium ions.

* * * * *